United States Patent
Annis

(10) Patent No.: US 7,442,799 B2
(45) Date of Patent: Oct. 28, 2008

(54) PREPARATION AND USE OF 2-SUBSTITUTED-5-OXO-3-PYRAZOLIDINE-CARBOXYLATES

(75) Inventor: Gary David Annis, Landenberg, PA (US)

(73) Assignee: E.I. du Pont de Nemours and Company, Wilmington, DE (US)

( * ) Notice: Subject to any disclaimer, the term of this patent is extended or adjusted under 35 U.S.C. 154(b) by 539 days.

(21) Appl. No.: 10/546,165

(22) PCT Filed: Mar. 25, 2004

(86) PCT No.: PCT/US2004/009188

§ 371 (c)(1), (2), (4) Date: Aug. 16, 2005

(87) PCT Pub. No.: WO2004/087689

PCT Pub. Date: Oct. 14, 2004

(65) Prior Publication Data

US 2007/0021468 A1    Jan. 25, 2007

Related U.S. Application Data

(60) Provisional application No. 60/457,561, filed on Mar. 26, 2003.

(51) Int. Cl.
*C07D 401/04* (2006.01)
*C07D 231/04* (2006.01)

(52) U.S. Cl. .............. 546/276.1; 546/268.1; 546/275.4; 548/356.1; 548/369.4

(58) Field of Classification Search .............. 546/268.1, 546/276.1; 548/356.1, 369.4
See application file for complete search history.

(56) References Cited

U.S. PATENT DOCUMENTS

| | | | |
|---|---|---|---|
| 3,153,654 A | 10/1964 | Ficken et al. | |
| 6,965,032 B2 * | 11/2005 | Freudenberger | 546/275.4 |
| 7,038,057 B2 * | 5/2006 | Annis et al. | 546/268.1 |
| 7,227,025 B2 * | 6/2007 | Freudenberger et al. | 546/275.4 |
| 7,335,780 B2 * | 2/2008 | Annis | 548/379.1 |

FOREIGN PATENT DOCUMENTS

| | | |
|---|---|---|
| EP | 344963 | 12/1989 |
| WO | WO 98/17273 | 4/1998 |
| WO | WO 00/69808 | 11/2000 |
| WO | WO 03/015519 | 2/2003 |

OTHER PUBLICATIONS

U. Aeberhard et al., Structure and Chemistry of Malonylmethyl- and Succinyl-Radicals, The Search for Homolytic 1,2-Rearrangements, HELV. CHIM, ACTA, 1983, 66(8), 2740-2759.
A.L. Gutman, Rearrangement During Bromination of Succinate Half Ester, Synthetic Communications 1985, 15(5), 459-462.
J.E. Baldwin et al., Total Synthesis of Antitumor Agent AT-125,(aS,SS)-a-Amino-3-Chloro-4,5-Dihydro-5-Isoxazoleacetic Acid, Tetrahedron 1985, 45(22), 5241-5260.
S.C. Arnold et al., Synthesis of Stereoregular Poly(Alkyl Malolactonates), Makromoll. Chem. Macromol. Symp., 1986, 6,285-303.
K.Fujishiro et al., Synthesis and Ring-Opening Polymerization of Optically Pure Mesogenic Malolactonates, Liquid Crystals, 1992, 12(3), 417-429.
M.C. Bobin, Les Derives De L'Acide, x, z-Diphenyl Z'-Chlorosuccinique, Comptes Rendus Acad. Sci, Paris, 1964, 258, 949-950.
De Amici et al., Nitrile Oxides in Medicinal Chemistry, Chemoenzymatic Synthesis of Chiral Heterocyclic Derivatives, J. Org. Chem., vol. 57, No. 10, 1992, pp. 2825-2829.
Database Beilstein Institute for Organic Chemistry, Frankfurt-Main, De; 1957, XP 002290996 Database Accession No. BRN 249955 Reaction ID 530690 (Abstract Re Bowman et al.).
Database Beilstein Institute for Organic Chemistry, Frankfurt-Main, De; 1989, XP 002291009 Database Accession No. BRN 2597730 (Abstract Re: Bobin et al.).

* cited by examiner

*Primary Examiner*—Golam M Shameem

(57) ABSTRACT

A method is disclosed for preparing a 2-substituted-5-oxo-3-pyrazolidinecarboxylate compound of Formula I. The method comprises contacting a succinic acid derivative of the formula $R^1OC(O)C(H)(X)C(R^{2a})(R^{2b})C(O)Y$ (i.e. Formula II) wherein X and Y are leaving groups and L, $R^1$, $R^{2a}$ and $R^{2b}$ are as defined in the disclosure, with a substituted hydrazine of the formula $LNHNH_2$ (i.e. Formula III) in the presence of a suitable acid scavenger and solvent. Also disclosed is the preparation of compounds of Formula IV wherein $X^1$, $R^6$, $R^7$, $R^{8a}$, $R^{8b}$, $R^9$, and n are as defined in the disclosure. Also disclosed is a composition comprising on a weight basis about 20 to 99% of the compound of Formula II wherein $R^1$, $R^{2a}$, $R^{2b}$, $R^3$, $R^4$ and $R^5$ are as defined in the disclosure; X is Cl, Br or I; and Y is F, Cl, Br or I; provided that when $R^{2a}$ and $R^{2b}$ are each H, and X and Y are each Cl then $R^1$ is other than benzyl and when $R^{2a}$ and $R^{2b}$ are each phenyl, and X and Y are each Cl, then $R^1$ is other than methyl or ethyl. Also disclosed is a crystalline composition comprising at least about 90% by weight of the compound of the formula $R^1OC(O)C(H)(X)C(R^{2a})(R^{2b})CO_2H$ (i.e. Formula VI) wherein $R^{2a}$ and $R^{2b}$ are H, X is Br and $R^1$ is methyl.

13 Claims, No Drawings

PREPARATION AND USE OF 2-SUBSTITUTED-5-OXO-3-PYRAZOLIDINE-CARBOXYLATES

This application represents a national filing under 35 usc 371 of International Application No. PCT/US2004/009188 filed Mar. 25, 2004 and claims priority of U.S. Provisional Application No. 60/457,56 1 filed Mar. 26, 2003.

BACKGROUND OF THE INVENTION

A need exists for additional methods to prepare 2-substituted-5-oxo-3-pyrazolidinecarboxylates. Such compounds include useful intermediates for the preparation of crop protection agents, pharmaceuticals, photographic developers and other fine chemicals. U.S. Pat. No. 3,153,654 and PCT Publication WO 03/015519 describe the preparation of 2-substituted-5-oxo-3-pyrazolidinecarboxylates by condensation of maleate or fumarate esters with substituted hydrazines in the presence of a base. However, alternative methods providing potentially greater yields are still needed.

SUMMARY OF THE INVENTION

This invention relates to a method for preparing a 2-substituted-5-oxo-3-pyrazolidinecarboxylate compound of Formula I

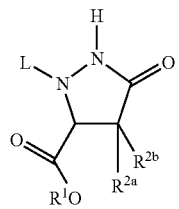

wherein
L is H, optionally substituted aryl, optionally substituted tertiary alkyl, —C(O)$R^3$, —S(O)$_2R^3$ or —P(O)($R^3$)$_2$;
$R^1$ is an optionally substituted carbon moiety;
$R^{2a}$ is H, O$R^4$ or an optionally substituted carbon moiety;
$R^{2b}$ is H or an optionally substituted carbon moiety;
each $R^3$ is independently O$R^5$, N($R^5$)$_2$ or an optionally substituted carbon moiety;
$R^4$ is an optionally substituted carbon moiety; and
each $R^5$ is selected from optionally substituted carbon moieties;

the method comprising contacting a succinic acid derivative of Formula II

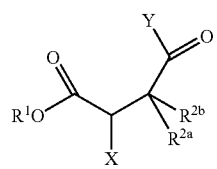

wherein
X is a leaving group; and
Y is a leaving group;

with a substituted hydrazine of Formula III $$LNHNH_2 \qquad III$$

in the presence of a suitable acid scavenger and solvent.

This invention also relates to a method of preparing a compound of Formula IV,

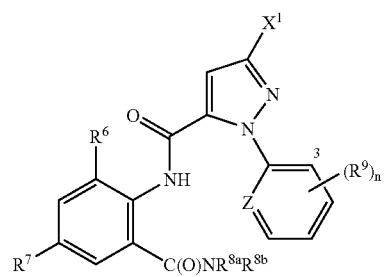

wherein
$X^1$ is halogen;
$R^6$ is $CH_3$, F, Cl or Br;
$R^7$ is P, Cl, Br, I, CN or $CF_3$;
$R^{8a}$ is H or $C_1$-$C_4$ alkyl;
$R^{8b}$ is H or $CH_3$;
each $R^9$ is independently $C_1$-$C_4$ alkyl, $C_2$-$C_4$ alkenyl, $C_2$-$C_4$ alkynyl, $C_3$-$C_6$ cycloalkyl, $C_1$-$C_4$ haloalkyl, $C_2$-$C_4$ haloalkenyl, $C_2$-$C_4$ haloalkynyl, $C_3$-$C_6$ halocycloalkyl, halogen, CN, $NO_2$, $C_1$-$C_4$ alkoxy, $C_1$-$C_4$ haloalkoxy, $C_1$-$C_4$ alkylthio, $C_1$-$C_4$ alkylsulfinyl, $C_1$-$C_4$ alkylsulfonyl, $C_1$-$C_4$ alkylamino, $C_2$-$C_8$ dialkylamino, $C_3$-$C_6$ cycloalkylamino, ($C_1$-$C_4$ alkyl)($C_3$-$C_6$ cycloalkyl) amino, $C_2$-$C_4$ alkylcarbonyl, $C_2$-$C_6$ alkoxycarbonyl, $C_2$-$C_6$ alkylaminocarbonyl, $C_3$-$C_8$ dialkylaminocarbonyl or $C_3$-$C_6$ trialkylsilyl;
Z is N or C$R^{10}$;
$R^{10}$ is H or $R^9$; and
n is an integer from 0 to 3 using a compound of Formula Ia

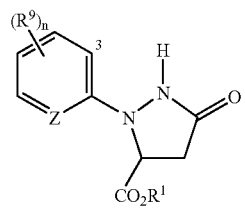

wherein $R^1$ is an optionally substituted carbon moiety.

This method is characterized by preparing the compound of Formula Ia (i.e. a subgenus of Formula I) by the method as indicated above.

This invention further provides a composition comprising on a weight basis about 20 to 99% of the compound of Formula II wherein $R^1$, $R^{2a}$, $R^{2b}$, $R^3$, $R^4$ and $R^5$ are as above; X is Cl, Br or I; and Y is F, Cl, Br or I; provided that when $R^{2a}$ and $R^{2b}$ are each H, and X and Y are each Cl then $R^1$ is other than benzyl and when $R^{2a}$ and $R^{2b}$ are each phenyl, and X and Y are each Cl, then $R^1$ is other than methyl or ethyl.

This invention further provides a crystalline composition comprising at least about 90% by weight of the compound of Formula VI

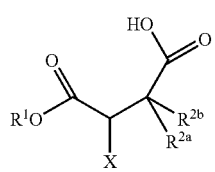

VI wherein $R^{2a}$ and $R^{2b}$ are H, X is Br and $R^1$ is methyl.

DETAILED DESCRIPTION OF THE INVENTION

In the recitations herein, the term "carbon moiety" refers to a radical comprising a carbon atom linking the radical to the remainder of the molecule. As the substituents $R^1$, $R^{2a}$, $R^{2b}$, $R^3$, $R^4$ and $R^5$ are separated from the reaction center, they can encompass a great variety of carbon-based groups preparable by modern methods of synthetic organic chemistry. Also the substituent L can encompass in addition to hydrogen a wide range of radicals selected from optionally substituted aryl, optionally substituted tertiary alkyl, —C(O)$R^3$, —S(O)$_2R^3$ or —P(O)($R^3$)$_2$, which stereoelectronically align with the cyclization regiochemistry of the method of the present invention. The method of this invention is thus generally applicable to a wide range of starting compounds of Formula II and product compounds of Formula I.

"Carbon moiety" thus includes alkyl, alkenyl and alkynyl, which can be straight-chain or branched. "Carbon moiety" also includes carbocyclic and heterocyclic rings, which can be saturated, partially saturated, or completely unsaturated. Furthermore, unsaturated rings can be aromatic if Hückel's rule is satisfied. The carbocyclic and heterocyclic rings of a carbon moiety can form polycyclic ring systems comprising multiple rings connected together. The term "carbocyclic ring" denotes a ring wherein the atoms forming the ring backbone are selected only from carbon. The term "heterocyclic ring" denotes a ring wherein at least one of the ring backbone atoms is other than carbon. "Saturated carbocyclic" refers to a ring having a backbone consisting of carbon atoms linked to one another by single bonds; unless otherwise specified, the remaining carbon valences are occupied by hydrogen atoms. The term "aromatic ring system" denotes fully unsaturated carbocycles and heterocycles in which at least one ring in a polycyclic ring system is aromatic. Aromatic indicates that each of ring atoms is essentially in the same plane and has a p-orbital perpendicular to the ring plane, and in which (4n+2) π electrons, when n is 0 or a positive integer, are associated with the ring to comply with Hückel's rule. The term "aromatic carbocyclic ring system" includes fully aromatic carbocycles and carbocycles in which at least one ring of a polycyclic ring system is aromatic. The term "nonaromatic carbocyclic ring system" denotes fully saturated carbocycles as well as partially or fully unsaturated carbocycles wherein none of the rings in the ring system are aromatic. The terms "aromatic heterocyclic ring system" and "heteroaromatic ring" include fully aromatic heterocycles and heterocycles in which at least one ring of a polycyclic ring system is aromatic. The term "nonaromatic heterocyclic ring system" denotes fully saturated heterocycles as well as partially or fully unsaturated heterocycles wherein none of the rings in the ring system are aromatic. The term "aryl" denotes a carbocyclic or heterocyclic ring or ring system in which at least one ring is aromatic, and the aromatic ring provides the connection to the remainder of the molecule.

The carbon moieties specified for $R^1$, $R^{2a}$, $R^{2b}$, $R^3$, $R^4$ and $R^5$ and the aryl and tertiary alkyl radicals specified for L are optionally substituted. The term "optionally substituted" in connection with these carbon moieties refers to carbon moieties that are unsubstituted or have at least one non-hydrogen substituent. Similarly, the term "optionally substituted" in connection with aryl and tertiary aryl refers to aryl and tertiary alkyl radicals that are unsubstituted or have a least on non-hydrogen substituent. Illustrative optional substituents include alkyl, alkenyl, cycloalkyl, cycloalkenyl, aryl, hydroxycarbonyl, formyl, alkylcarbonyl, alkenylcarbonyl, alkynylcarbonyl, alkoxycarbonyl, hydroxy, alkoxy, alkenyloxy, alkynyloxy, cycloalkoxy, aryloxy, alkylthio, alkenylthio, alkynylthio, cycloalkylthio, arylthio, alkylsulfinyl, alkenylsulfinyl, alkynylsulfinyl, cycloalkylsulfinyl, arylsulfinyl, alkylsulfonyl, alkenylsulfonyl, alkynylsulfonyl, cycloalkylsulfonyl, arylsulfonyl, amino, alkylamino, alkenylamino, alkynylamino, arylamino, aminocarbonyl, alkylaminocarbonyl, alkenylaminocarbonyl, alkynylaminocarbonyl, arylaminocarbonyl, alkylaminocarbonyl, alkenylaminocarbonyl, alkynylaminocarbonyl, arylaminocarbonyloxy, alkoxycarbonylamino, alkenyloxycarbonylamino, alkynyloxycarbonylamino and aryloxy-carbonylamino, each further optionally substituted; and halogen, cyano and nitro. The optional further substituents are independently selected from groups like those illustrated above for the substituents themselves to give additional substituent radicals for L, $R^1$, $R^{2a}$, $R^{2b}$, $R^3$, $R^4$ and $R^5$ such as haloalkyl, haloalkenyl and haloalkoxy. As a further example, alkylamino can be further substituted with alkyl, giving dialkylamino. The substituents can also be tied together by figuratively removing one or two hydrogen atoms from each of two substituents or a substituent and the supporting molecular structure and joining the radicals to produce cyclic and polycyclic structures fused or appended to the molecular structure supporting the substituents. For example, tying together adjacent hydroxy and methoxy groups attached to, for example, a phenyl ring gives a fused dioxolane structure containing the linking group —O—CH$_2$—O—. Tying together a hydroxy group and the molecular structure to which it is attached can give cyclic ethers, including epoxides. Illustrative substituents also include oxygen, which when attached to carbon forms a carbonyl function. Similarly, sulfur when attached to carbon forms a thiocarbonyl function. Within the L, $R^1$, $R^{2a}$, $R^{2b}$, $R^3$, $R^4$ or $R^5$ moieties, tying together substituents can form cyclic and polycyclic structures. Also illustrative of $R^1$, $R^{2a}$ and $R^{2b}$ are embodiments wherein at least two of the $R^1$, $R^{2a}$ and $R^{2b}$ moieties are contained in the same radical (i.e. a ring system is formed). As the pyrazolidine moiety constitutes one ring, the $R^1$ moiety contained in the same radical as $R^{2a}$ (or O$R^4$) or $R^{2b}$ would result in a fused bicyclic or polycyclic ring system. Two $R^{2a}$ and $R^{2b}$ moieties contained in the same radical would result in a spiro ring system.

As referred to herein, "alkyl", used either alone or in compound words such as "alkylthio" or "haloalkyl" includes straight-chain or branched alkyl, such as, methyl, ethyl, n-propyl, i-propyl, or the different butyl, pentyl or hexyl isomers. "Tertiary alkyl" denotes a branched alkyl radical wherein the carbon atom linked to the remainder of the molecule is also attached to three carbon atoms in the radical. Examples of "tertiary alkyl" include —C(CH$_3$)$_3$, —C(CH$_3$)$_2$CH$_2$CH$_3$ and —C(CH$_3$)(CH$_2$CH$_3$)(CH$_2$)$_2$CH$_3$. "Alkenyl" includes straight-chain or branched alkenes such as ethenyl, 1-propenyl, 2-propenyl, and the different butenyl, pentenyl and hexenyl isomers. "Alkenyl" also includes polyenes such as 1,2-propadienyl and 2,4-hexadienyl. "Alkynyl" includes straight-chain or branched alkynes such as ethynyl, 1-propynyl, 2-propynyl and the different butynyl, pentynyl and hexynyl isomers. "Alkynyl" can also include moieties comprised of multiple triple bonds such as 2,5-hexadiynyl. "Alkoxy" includes, for example, methoxy, ethoxy, n-propyloxy, isopropyloxy and the different butoxy, pentoxy and hexyloxy isomers. "Alkenyloxy"includes straight-chain or branched alkenyloxy moieties. Examples of "alkenyloxy" include $H_2C=CHCH_2O$, $(CH_3)_2C=CHCH_2O$, $(CH_3)CH=CHCH_2O$, $(CH_3)CH=C(CH_3)CH_2O$ and $CH_2=CHCH_2CH_2O$. "Alkynyloxy" includes straight-chain or branched alkynyloxy moieties. Examples of "alkynyloxy" include $HC\equiv CCH_2O$, $CH_3C\equiv CCH_2O$ and $CH_3C\equiv CCH_2CH_2O$. "Alkylthio" includes branched or straight-chain alkylthio moieties such as methylthio, ethylthio, and the different propylthio, butylthio, pentylthio and hexylthio isomers. "Alkylsulfinyl" includes both enantiomers of an alkylsulfinyl group. Examples of "alkylsulfinyl" include $CH_3S(O)$, $CH_3CH_2S(O)$, $CH_3CH_2CH_2S(O)$, $(CH_3)_2CHS(O)$ and the different butylsulfinyl, pentylsulfinyl and hexylsulfinyl isomers. Examples of "alkylsulfonyl" include $CH_3S(O)_2$, $CH_3CH_2S(O)_2$, $CH_3CH_2CH_2S(O)_2$, $(CH_3)_2CHS(O)_2$ and the different butylsulfonyl, pentylsulfonyl and hexylsulfonyl isomers. "Alkylamino", "alkenylthio", "alkenylsulfinyl", "alkenylsulfonyl", "alkynylthio", "alkynylsulfinyl", "alkynylsulfonyl", and the like, are defined analogously to the above examples. Examples of "alkylcarbonyl" include $C(O)CH_3$, $C(O)CH_2CH_2CH_3$ and $C(O)CH(CH_3)_2$. Examples of "alkoxycarbonyl" include $CH_3OC(=O)$, $CH_3CH_2OC(=O)$, $CH_3CH_2CH_2OC(=O)$, $(CH_3)_2CHOC(=O)$ and the different butoxy- or pentoxycarbonyl isomers. "Cycloalkyl" includes, for example, cyclopropyl, cyclobutyl, cyclopentyl, and cyclohexyl. The term "cycloalkoxy" includes the same groups linked through an oxygen atom such as cyclopentyloxy and cyclohexyloxy. "Cycloalkylamino" means the amino nitrogen atom is attached to a cycloalkyl radical and a hydrogen atom and includes groups such as cyclopropylamino, cyclobutylamino, cyclopentylamino and cyclohexylamino. "(Alkyl)(cycloalkyl)amino" means a cycloalkylamino group where the hydrogen atom is replaced by an alkyl radical; examples include groups such as (methyl)(cyclopropyl)amino, (butyl)(cyclobutyl)amino, (propyl)cyclopentylamino, (methyl)cyclohexylamino and the like. "Cycloalkenyl" includes groups such as cyclopentenyl and cyclohexenyl as well as groups with more-than one double bond such as 1,3- and 1,4-cyclohexadienyl.

The term "halogen", either alone or in compound words such as "haloalkyl", includes fluorine, chlorine, bromine or iodine. The term "1-2 halogen" indicates that one or two of the available positions for that substituent may be halogen which are independently selected. Further, when used in compound words such as "haloalkyl", said alkyl may be partially or fully substituted with halogen atoms which may be the same or different. Examples of "haloalkyl" include $F_3C$, $ClCH_2$, $CF_3CH_2$ and $CF_3CCl_2$.

The term "sulfonate" refers to radicals comprising a $-OS(O)_2-$ wherein the sulfur atom is bonded to a carbon moiety, and the oxygen atom is bonded to the remainder of the molecule and thus serves as the attachment point for the sulfonate radical. Commonly used sulfonates include $-OS(O)_2Me$, $-OS(O)_2Et$, $-OS(O)_2-n-Pr$, $-OS(O)_2CF_3$, $-OS(O)_2Ph$ and $-S(O)_2Ph-4-Me$.

The total number of carbon atoms in a substituent group is indicated by the "$C_i$-$C_j$"prefix where i and j are, for example, numbers from 1 to 3; e.g., $C_1$-$C_3$ alkyl designates methyl through propyl.

Although there is no definite limit to the sizes of Formulae I, II and III suitable for the processes of the invention, typically Formula I comprises 5-100, more commonly 5-50,, and most commonly 5-25 carbon atoms, and 5-25, more commonly 5-15, and most commonly 5-10 heteroatoms. Typically Formula II comprises 5-50, more commonly 5-25, and most commonly 5-12 carbon atoms, and 5-15, more commonly 5-10, and most commonly 5-7 heteroatoms. Typically Formula III comprises 0-50, more commonly 6-25, and most commonly 6-13 carbon atoms, and 2-12, more commonly 2-7, and most commonly 2-5 heteroatoms. The heteroatoms are commonly selected from halogen, oxygen, sulfur, nitrogen and phosphorus. Three heteroatoms in Formulae I and II are the two oxygen atoms in the carboxylate ester group ($R^1OC(O)-$) and the oxygen atom in the other carbonyl radical. Two heteroatoms in Formulae I and III are the two nitrogen atoms in the pyrazoline ring and the precursor hydrazine. X and Y typically each comprise at least one heteroatom.

Although there is no definite limit to the size of $R^1$, $R^{2a}$, $R^{2b}$, $R^3$, $R^4$ and $R^5$, optionally substituted alkyl moieties of $R^1$, $R^{2a}$, $R^{2b}$, $R^3$, $R^4$ and $R^5$ commonly include 1 to 6 carbon atoms, more commonly 1 to 4 carbon atoms and most commonly 1 to 2 carbon atoms in the alkyl chain. Optionally substituted alkenyl and alkynyl moieties of $R^1$, $R^{2a}$, $R^{2b}$, $R^3$, $R^4$ and $R^5$ commonly include 2 to 6 carbon atoms, more commonly 2 to 4 carbon atoms and most commonly 2 to 3 carbon atoms in the alkenyl or alkynyl chain. Optionally substituted tertiary alkyl moieties of L commonly include 4 to 10 carbon atoms, more commonly 4 to 8 carbon atoms and most commonly 4 to 6 carbon atoms.

As indicated above, the carbon moieties of $R^1$, $R^{2a}$, $R^{2b}$, $R^3$, $R^4$ and $R^5$ may be (among others) an aromatic ring or ring system. Also the aryl moiety of L is an aromatic ring or ring system. Examples of aromatic rings or ring systems include a phenyl ring, 5- or 6-membered heteroaromatic rings, aromatic 8-, 9- or 10-membered fused carbobicyclic ring. systems and aromatic 8-, 9- or 10-membered fused heterobicyclic ring systems wherein each ring or ring system is optionally substituted. The term "optionally substituted" in connection with these $R^1$, $R^{2a}$, $R^{2b}$, $R^3$, $R^4$ and $R^5$ carbon moieties and the aryl moiety of L refers to carbon moieties which are unsubstituted or have at least one non-hydrogen substituent. These carbon moieties may be substituted with as many optional substituents as can be accommodated by replacing a hydrogen atom with a non-hydrogen substituent on any available carbon or nitrogen atom. Commonly, the number of optional substituents (when present) ranges from one to four. An example of phenyl optionally substituted with from one to four substituents is the ring illustrated as U-1 in Exhibit 1, wherein $R^v$ is any non-hydrogen substituent and r is an integer from 0 to 4. Examples of aromatic 8-, 9- or 10-membered fused carbobicyclic ring systems optionally substituted with from one to four substituents include a naphthyl group optionally substituted with from one to four substituents illustrated as U-85 and a 1,2,3,4-tetrahydronaphthyl group optionally substituted with from one to four substituents illustrated as U-86 in Exhibit 1, wherein $R^v$ is any substituent and r is an integer from 0 to 4. Examples of 5- or 6-membered heteroaromatic rings optionally substituted with from one to four substituents include the rings U-2 through U-53 illustrated in Exhibit 1 wherein $R^v$ is any substituent and r is an integer from 1 to 4. Examples of aromatic 8-, 9- or 10-membered fused heterobicyclic ring systems optionally substituted with from one to four substituents include U-54 through U-84 illustrated in Exhibit 1 wherein $R^v$ is any substituent, for example a substituent such as $R^9$, and r is an integer from 0 to 4.. Other examples of L, $R^1$, $R^{2a}$, $R^{2b}$, $R^3$, $R^4$ and $R^5$ include a benzyl group optionally substituted with from one to four substituents illustrated as U-87 and a benzoyl group optionally substituted with from one to four substituents illustrated as U-88 in Exhibit 1, wherein $R^v$ is any substituent and r is an integer from 0 to 4.

Although $R^v$ groups are shown in the structures U-1 through U-85, it is noted that they do not need to be present since they are optional substituents. The nitrogen atoms that require substitution to fill their valence are substituted with H or $R^v$. Note that some U groups can only be substituted with less than 4 $R^v$ groups (e.g., U-14, U-15, U-18 through U-21 and U-32 through U-34 can only be substituted with one $R^v$). Note that when the attachment point between $(R^v)_r$ and the U group is illustrated as floating, $(R^v)_r$ can be attached to any available carbon atom or nitrogen atom of the U group. Note that when the attachment point on the U group is illustrated as floating, the U group can be attached to the remainder of Formulae I, II and III through any available carbon of the U group by replacement of a hydrogen atom.

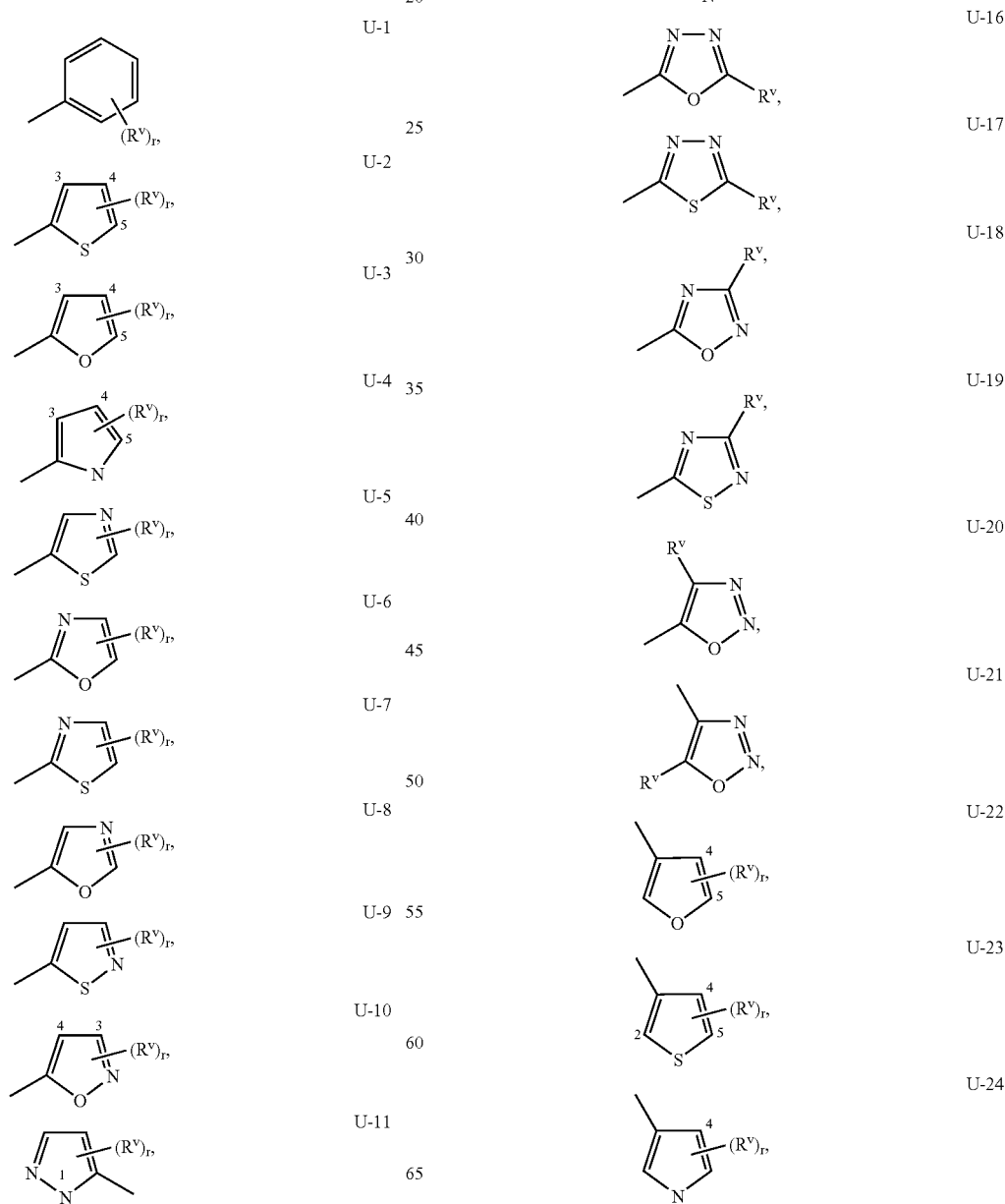

-continued
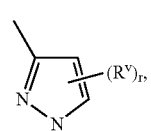 U-25
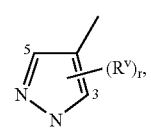 U-26
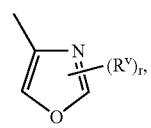 U-27
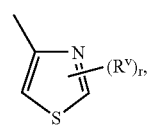 U-28
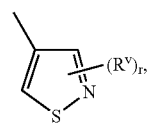 U-29
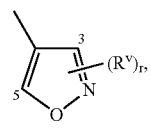 U-30
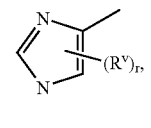 U-31
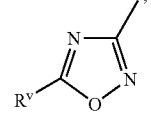 U-32
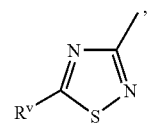 U-33
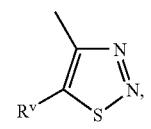 U-34
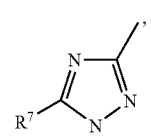 U-35
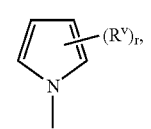 U-36
-continued
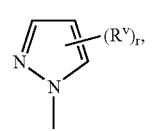 U-37
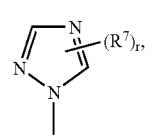 U-38
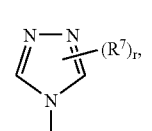 U-39
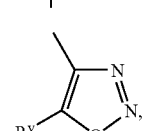 U-40
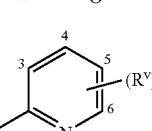 U-41
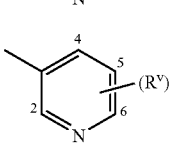 U-42
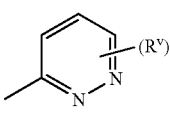 U-43
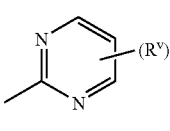 U-44
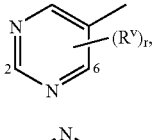 U-45
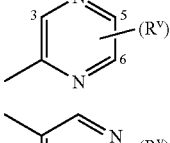 U-46
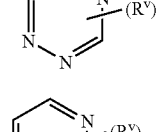 U-47
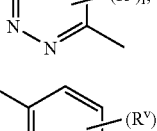 U-48
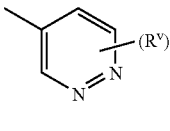 U-49

Chemical structure figures U-50 through U-73 (no extractable text content beyond labels).

As indicated above, the carbon moieties of $R^1$, $R^{2a}$, $R^{2b}$, $R^3$, $R^4$ and $R^5$ may be (among others) saturated or partially saturated carbocyclic and heterocyclic rings, which can be further optionally substituted. The term "optionally substituted" in connection with these $R^1$, $R^{2a}$, $R^{2b}$, $R^3$, $R^4$ and $R^5$ carbon moieties refers to carbon moieties which are unsubstituted or have at least one non-hydrogen substituent. These carbon moieties may be substituted with as many optional substituents as can be accommodated by replacing a hydrogen atom with a non-hydrogen substituent on any available carbon or nitrogen atom. Commonly, the number of optional substituents (when present) ranges from one to four. Examples of saturated or partially saturated carbocyclic rings include optionally substituted $C_3$-$C_8$ cycloalkyl and optionally substituted $C_3$-$C_8$ cycloalkyl. Examples of saturated or partially saturated heterocyclic rings include 5- or 6-membered nonaromatic heterocyclic rings optionally including one or two ring members selected from the group consisting of C(=O), SO or $S(O)_2$, optionally substituted. Examples of such $R^1$, $R^{2a}$, $R^{2b}$, $R^3$, $R^4$ and $R^5$ carbon moieties include those illustrated as G-1 through G-35 in Exhibit 2. Note that when the attachment point on these G groups is illustrated as floating, the G group can be attached to the remainder of Formulae I and II through any available carbon or nitrogen of the G group by replacement of a hydrogen atom. The optional substituents can be attached to any available carbon or nitrogen by replacing a hydrogen atom (said substituents are not illustrated in Exhibit 2 since they are optional substituents). Note that when G comprises a ring selected from G-24 through G-31, G-34 and G-35, $Q^2$ may be selected from O, S, NH or substituted N.

-continued
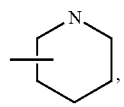 G-7
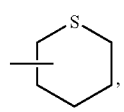 G-8
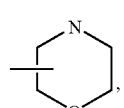 G-9
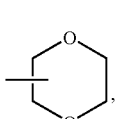 G-10
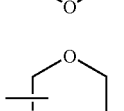 G-11
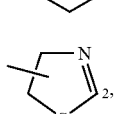 G-12
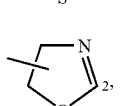 G-13
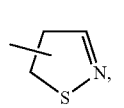 G-14
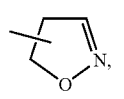 G-15
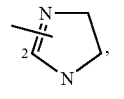 G-16
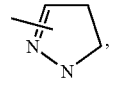 G-17
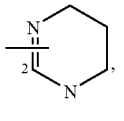 G-18
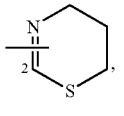 G-19
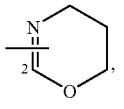 G-20
-continued
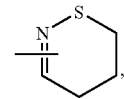 G-21
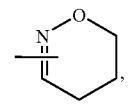 G-22
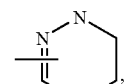 G-23
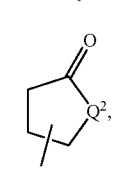 G-24
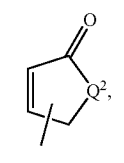 G-25
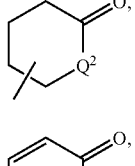 G-26
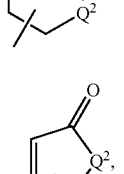 G-27
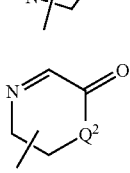 G-28
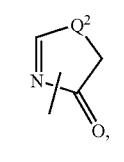 G-29
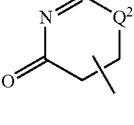 G-30
 G-31
G-32

-continued

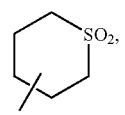
G-33

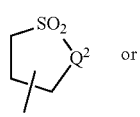 or
G-34

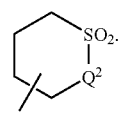
G-35

It is noted that the carbon moieties of $R^1$, $R^{2a}$, $R^{2b}$, $R^3$, $R^4$ and $R^5$ and the aryl and tertiary alkyl moieties of L may be optionally substituted. As noted above, the $R^1$, $R^{2a}$, $R^{2b}$, $R^3$, $R^4$ and $R^5$ carbon moieties may commonly comprise, among other groups, a U group or a G group further optionally substituted with from one to four substituents. The L aryl moiety may commonly comprise, among other groups, a U group further optionally substituted with from one to four substituents. Thus the $R^1$, $R^{2a}$, $R^{2b}$, $R^3$, $R^4$ and $R^5$ carbon moieties may comprise a U group or a G group selected from U-1 through U-88 or G-1 through G-35, and further substituted with additional substituents including one to four U or G groups (which may be the same or different) with both the core U or G group and substituent U or G groups optionally further substituted. The L moiety may comprise a U group selected from U-1 through U-88 or a tertiary alkyl radical, and further substituted with additional substituents including one to four U or G groups (which may be the same or different) with both the core U group (or tertiary alkyl radical) and the substituent U or G groups optionally further substituted. Of particular note are L carbon moieties comprising a U group optionally substituted with from one to three additional substituents. For example, L can be U-11, in which an $R^v$ attached to the 1-nitrogen is the group U-41 as shown in Exhibit 3.

Exhibit 3

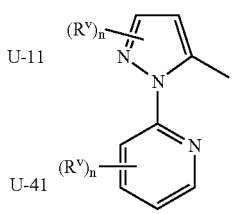

As generally defined herein, a "leaving group" denotes an atom or group of atoms displaceable in a nucleophilic substitution reaction. More particularly, "leaving group" refers to substituents X and Y, which are displaced in the reaction according to the method of the present invention. As is well known to those skilled in the art, a nucleophilic reaction leaving group carries the bonding electron pair with it as it is displaced. Accordingly the facility of leaving groups for displacement generally correlates with the stability of the leaving group species carrying the bonding electron pair. For this reason, strong leaving groups (e.g., Br, Cl, I and sulfonates such as $OS(O)_2CH_3$) give displaced species that can be regarded as the conjugate bases of strong acids. Because of its high electronegativity, fluoride (F) can also be a strong leaving group from $sp^2$ carbon centers such as in acyl fluorides.

According to the method of the present invention a compound of Formula I is prepared by reacting a compound of Formula II with a compound of Formula III as shown in Scheme 1.

Scheme 1

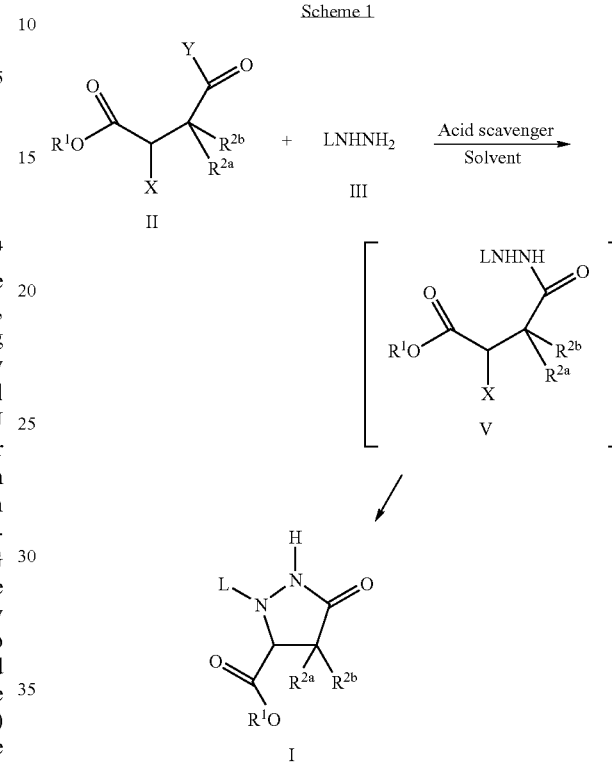

wherein $R^1$, $R^{2a}$, $R^{2b}$, L, X and Y are as previously defined.

Although the intermediate compound of Formula V can sometimes be isolated, it is usually not, because it spontaneously cyclizes to the corresponding compound of Formula I at room temperature. The cyclization is sometimes slow at room temperature, but proceeds at useful rates at elevated temperatures.

While the 5-oxo-pyrazoline product of Formula I is shown in Scheme 1 as a lactam, one skilled in the art recognizes that this is tautomeric with the lactol of Formula Ib as shown in Scheme 2.

Scheme 2

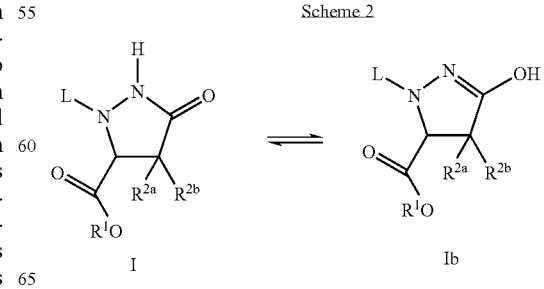

wherein $R^1$, $R^{2a}$, $R^{2b}$ and L are as previously, defined.

As these tautomers readily equilibrate, they are regarded as chemically equivalent. Unless otherwise indicated, all references to Formula I herein are to be construed to include also Formula Ib.

Preferred for reason of ease of synthesis, better yield, higher purity, lower cost and/or product utility is the method of the present invention wherein: L is preferably H, optionally substituted aryl or optionally substituted tertiary alkyl. More preferably, L is H or optionally substituted aryl. Even more preferably, L is optionally substituted aryl. Most preferably, L is phenyl or pyridyl, each optionally substituted. $R^1$ is preferably $C_1$-$C_{16}$ alkyl, $C_1$-$C_{16}$ alkenyl or $C_1$-$C_{16}$ alkynyl, each optionally substituted with one or more substituents selected from halogen, $C_1$-$C_4$ alkoxy or phenyl. More preferably, $R^1$ is $C_1$-$C_4$ alkyl. Even more preferably, $R^1$ is $C_1$-$C_2$ alkyl. Most preferably, $R^1$ is methyl. Preferably, $R^{2a}$ is H or an optionally substituted carbon moiety. More preferably, $R^{2a}$ is H. Most preferably, $R^{2a}$ and $R^{2b}$ are each H. Preferably, each $R^3$ is independently selected from $OR^5$ or an optionally substituted carbon moiety. More preferably, each $R^3$ is independently selected from an optionally substituted carbon moiety. Even more preferably, each $R^3$ is independently selected from $C_1$-$C_6$ alkyl optionally substituted with one or more groups selected from halogen or $C_1$-$C_4$ alkoxy, or phenyl optionally substituted with 1-3 groups selected from halogen, $C_1$-$C_4$ alkyl or $C_1$-$C_4$ alkoxy. Most preferably, each $R^3$ is independently selected from $C_1$-$C_4$ alkyl, phenyl or 4-methylphenyl. Preferably, each $R^5$ is independently selected from $C_1$-$C_6$ alkyl optionally substituted with one or more groups selected from halogen or $C_1$-$C_4$ alkoxy. More preferably, each $R^5$ is independently selected from $C_1$-$C_4$ alkyl.

In the method of the present invention the leaving group Y of the starting compound of Formula II is first displaced to give the intermediate compound of Formula V, from which the leaving group X is displaced to give the final product of Formula I. Strong leaving groups are generally suitable for X and Y in the present method. Preferably leaving groups are selected for X and Y in view of their relative susceptibility to displacement so that leaving group Y is displaced before leaving group X. However, as nucleophilic substitution is inherently more rapid on acyl centers compared to the 2-position of esters, most combinations of strong leaving groups work well for X and Y in the present method. X is preferably Cl, Br, I or a sulfonate (e.g., $OS(O)_2CH_3$, $OS(O)_2CF_3$, $OS(O)_2Ph$, $OS(O)_2Ph$-4-Me). More preferably, X is Cl, Br or I. Even more preferably, X is Cl or Br. Most preferably, X is Br. Y is preferably F, Cl, Br or I. More preferably, Y is Cl or Br. Most preferably, Y is Cl. The combination of X being Br and Y being Cl is notable for rapid condensation according to the method of the present invention to give a compound of Formula I in high yield and regioselectivity.

The reaction is conducted in the presence of a suitable acid scavenger. Suitable acid scavengers for the method of the present invention include bases and also chemical compounds not typically considered bases but nevertheless capable of reacting with and consuming strong acids such as hydrogen chloride and hydrogen bromide. Nonbasic acid scavengers include epoxides such as propylene oxide and olefins such as 2-methylpropene. Bases include ionic bases and nonionic bases. Nonionic bases include organic amines. Organic bases providing best results include amines that are only moderately basic and nucleophilic, e.g., N,N-diethylaniline. Useful ionic bases include fluorides, oxides, hydroxides, carbonates, carboxylates and phosphates of alkali and alkaline earth metal elements. Examples include NaF, MgO, CaO, $LiHCO_3$, $Li_2CO_3$, LiOH, NaOAc, $NaHCO_3$, $Na_2CO_3$, $Na_2HPO_4$, $Na_3PO_4$, $KHCO_3$, $K_2CO_3$, $K_2HPO_4$ and $K_3PO_4$. Giving particularly good results are inorganic carbonate and phosphate bases comprising alkali metal elements (e.g., $LiHCO_3$, $Li_2CO_3$, $Li_2HPO_4$, $Li_3PO_4$, $NaHCO_3$, $Na_2CO_3$, $Na_2HPO_4$ and $Na_3PO_4$). Of these, preferred for their low cost as well as excellent results are $NaHCO_3$, $Na_2CO_3$, $Na_2HPO_4$ and $Na_3PO_4$. Particularly preferred is $NaHCO_3$ and $Na_3PO_4$. Most preferred is $NaHCO_3$. Preferably at least two equivalents of acid scavenger is employed in the method of the present invention. Typically about 2 to 2.5 equivalents of acid scavenger is used. For the reaction of relatively acidic hydrazines of Formula III wherein, for example, L is —$S(O)_2R^3$ it may be advantagous to add first an acid scavenger that is not a strong base to avoid deprotonating the hydrazine moiety of Formula III during the formation of the intermediate of Formula V and then add a strong base to deprotonate the hydrazine moiety of Formula V to accelerate the condensation to give the final product of Formula I.

Suitable solvents include polar aprotic solvents such as N,N-dimethylformamide, methyl sulfoxide, ethyl acetate, dichloromethane, acetonitrile and the like. Nitrile solvents such as acetonitrile, proprionitrile and butyronitrile often provide optimal yields and product purities. Particularly preferred for its low cost and excellent utility as solvent for the method of this invention is acetonitrile.

The method of the present invention can be conducted over a wide temperature range, but is typically conducted at temperatures between about −10 and 80° C. While the intermediate compound of Formula V can be formed at 80° C. or higher, the best yields and purities are often achieved by forming it at lower temperature, such as between about 0° C. and ambient temperature (e.g., about 15 to 25° C.). Typically during the addition of reactants the reaction mixture is cooled to a temperature of −5 to 5° C., most conveniently about 0° C. After the reactants have been combined, the temperature is typically increased to near ambient temperature. To then increase the rate of cyclization of the compound of Formula V to the compound of Formula I, a temperature in the range of about 30 to 80° C. is usually employed, more typically about 30 to 60° C., and most typically about 40° C. The product of Formula I can be isolated by the usual methods well known to those skilled in the art such as evaporation of solvent, chromatography and crystallization. Addition of an acid with a $pK_a$ in the range of 2 to 5 can buffer excess base and prevent saponification and degradation of the product of Formula I during isolation steps involving water and heat (such as removal of solvent by distillation). Acetic acid works well for this purpose. Also, addition of such acids as acetic acid to concentrated solutions of certain products of Formula I can promote their crystallization.

Preferred methods of this invention include the method wherein the starting compound of Formula II is Formula IIa, the starting compound of Formula III is Formula IIIa and the product compound of Formula I is Formula Ia as shown in Scheme 3 below.

Scheme 3

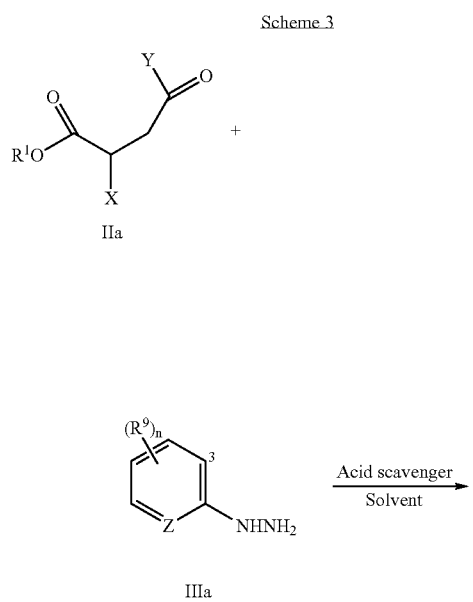

wherein $R^1$ is as defined for Formulae I and II;

X and Y are as defined for Formula II;

each $R^9$ is independently $C_1$-$C_4$ alkyl, $C_2$-$C_4$ alkenyl, $C_2$-$C_4$ alkynyl, $C_3$-$C_6$ cycloalkyl, $C_1$-$C_4$ haloalkyl, $C_2$-$C_4$ haloalkenyl, $C_2$-$C_4$ haloalkynyl, $C_3$-$C_6$ halocycloalkyl, halogen, CN, $NO_2$, $C_1$-$C_4$ alkoxy, $C_1$-$C_4$ haloalkoxy, $C_1$-$C_4$ alkylthio, $C_1$-$C_4$ alkylsulfinyl, $C_1$-$C_4$ alkylsulfonyl, $C_1$-$C_4$ alkylamino, $C_2$-$C_8$ dialkylamino, $C_3$-$C_6$ cycloalkylamino, ($C_1$-$C_4$ alkyl)($C_3$-$C_6$ cycloalkyl)amino, $C_2$-$C_4$ alkylcarbonyl, $C_2$-$C_6$ alkoxycarbonyl, $C_2$-$C_6$ alkylaminocarbonyl, $C_3$-$C_8$ dialkylaminocarbonyl or $C_3$-$C_6$ trialkylsilyl;

Z is N or $CR^{10}$;

$R^{10}$ is H or $R^9$; and n is an integer from 0 to 3.

One skilled in the art will recognize that Formula Ia is a subgenus of Formula I, Formula IIa is subgenus of Formula II, Formula IIIa is a subgenus of Formula III, and Formula Va is a subgenus of Formula V.

While a wide range of optionally substituted carbon moieties as already described are useful as $R^1$ in esters of Formula Ia for the method of Scheme 3, commonly $R^1$ is a radical containing up to 18 carbon atoms and selected from alkyl, alkenyl and alkynyl; and benzyl and phenyl, each optionally substituted with alkyl and halogen. Preferably $R^1$ is $C_1$-$C_4$ alkyl, more preferably $R^1$ is $C_1$-$C_2$ alkyl, and most preferably $R^1$ is methyl. Preferably X is Cl or Br, and more preferably X is Br. Preferably Y is Cl. Of note is the method shown in Scheme 3 wherein Z is N, n is 1 and $R^9$ is Cl or Br and is located at the 3-position.

As shown in Scheme 4, compounds of Formula II can be prepared by treating the corresponding carboxylic acids of Formula VI with the appropriate reagents to convert the hydroxy radical of the carboxylic acid function into a leaving group.

Scheme 4

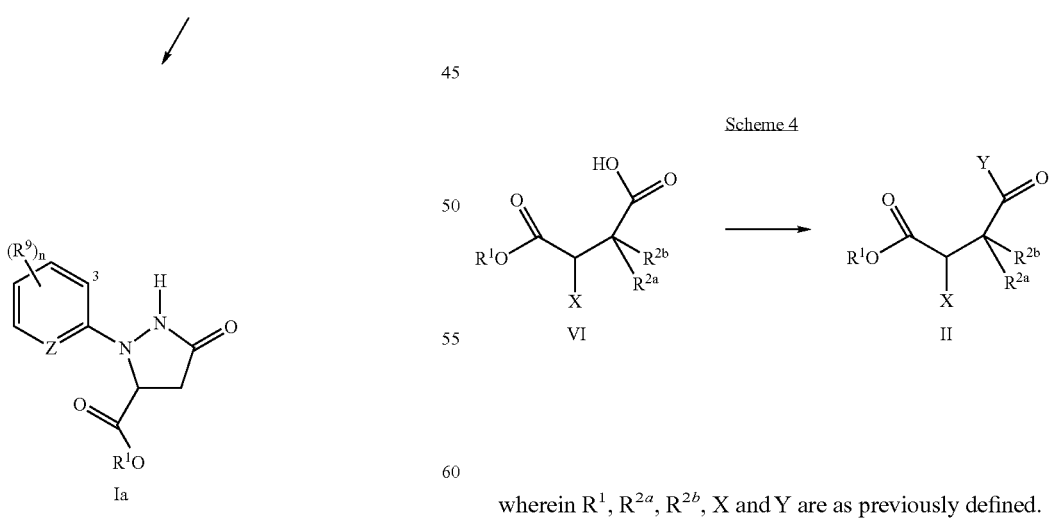

wherein $R^1$, $R^{2a}$, $R^{2b}$, X and Y are as previously defined.

For example, a compound of Formula IIb (i.e. Formula II wherein Y is Cl) can be prepared by contacting a corresponding carboxylic acid of Formula VI with a reagent for converting carboxylic acids to acyl chlorides, such as thionyl chloride ($S(O)Cl_2$) as shown in Scheme 5.

Scheme 5

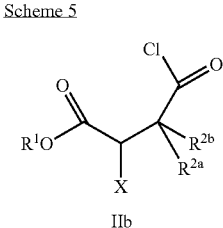

wherein $R^1$, $R^{2a}$, $R^{2b}$ and X are as previously defined.

The reaction of the carboxylic acid of Formula VI with thionyl chloride is typically conducted in the presence of a moderately polar aprotic solvent such as dichloromethane, 1,2-dichloroethane, benzene, chlorobenzene or toluene. The reaction can be catalyzed by addition of N,N-dimethylformamide. Typically the reaction temperature is in the range of about 30 to 80° C. When dichloromethane-is used as solvent, the reaction is conveniently conducted at about its boiling point of 40° C. Rapid removal of hydrogen chloride generated by the reaction is desirable and can be facilitated by boiling the solvent to limit the solubility of the hydrogen chloride. Because of its moderate boiling point, dichloromethane is preferred as a solvent.

Because of compounds of Formula VI can be easily and inexpensively converted to compounds of Formula II wherein Y is Cl (i.e. Formula IIb), Y being Cl is preferred for the method of the present invention. However, other leaving groups are also useful as Y in the present method. Compounds of Formula II wherein Y is a leaving group other than Cl can be prepared either directly from the corresponding compounds of Formula VI or from the compounds of Formula IIb by methods well known to those skilled in the art (see, for example, H. W. Johnson & D. E. Bublitz, *J. Am. Chem. Soc.* 1958, 80, 3150-3152 (VI to II (Y is Br)); G. Oláh et al., *Chem. Ber.* 1956, 89, 862-864 (IIb to II (Y is F)); R. N. Haszeldine, *J. Chem. Soc.* 1951, 584587 (IIb to II (Y is I))).

As discussed above, acyl halide compounds of Formula II are easily prepared from the corresponding carboxylic acids of Formula VI by contacting with thionyl chloride (for Y is Cl) or other reagents for Y being another halide, or by contacting a compound of Formula II wherein Y is Cl with the appropriate reagent to convert Y to another halogen. Even though acyl halide compounds of Formula II are easily prepared, they are less simply isolated in 100% concentration, because they are typically not crystalline and at reduced pressures commonly available for chemical manufacturing their boiling points are typically higher than their decomposition temperatures, thereby precluding distilling them. Although solvents can be removed from acyl halide compounds of Formula II by such methods as evaporation or distillation of the solvent at reduced pressure, typically sufficient solvent is entrained to cause the concentration of the Formula II compound to remain below 100%. However, the solvents used to prepare the compounds of Formula II are generally compatible with the method of the present invention, and therefore the method of the present invention works well starting with compositions of compounds of Formula II wherein the concentration of Formula II compound is less than 100%. Therefore a composition of Formula II compound useful for the method of the present invention typically also comprises a solvent, particularly a solvent used to prepare the Formula II compound. Typical solvents include dichloromethane, 1,2-dichloroethane, benzene, chlorobenzene or toluene. Typically said composition comprises about 20 to 99% of Formula II compound on a weight basis. Preferably said composition comprises about 40 to 99 weight % of Formula II compound. More preferably said composition comprises about 50 to 99 weight % of Formula II compound. Also preferably said composition comprises at least about 80% of Formula II compound based on the sum of the weight of the Formula II compound (including all stereoisomers) and the weights of regioisomers of the Formula II compound in the composition. (For this calculation, the weight of Formula II compound (including all stereoisomers) is divided by the sum of the weight of the Formula II compound (including all stereoisomers) and the weights of regioisomers of the Formula II compound, and then the resulting division quotient is multiplied by 100%. The regioisomers of Formula II involve, for example, interchanging the placement of X and $R^{2a}$ or $R^{2b}$.) More preferably said composition comprises at least about 90% of the Formula II compound based on the total weight of the Formula II compound and its regioisomers in the composition (i.e. the aforementioned sum of weights). Most preferably said composition comprises at least about 94% of Formula II compound based on the total weight of the Formula II compound and its regioisomers in the composition. Preferred is a composition comprising a compound of Formula II wherein Y is Cl and X is Cl, Br or I, preferably Cl or Br, and more preferably Br. Of note is a composition, including said preferred composition, comprising a compound of Formula II wherein when $R^{2a}$ and $R^{2b}$ are each H, and X and Y are each Cl then $R^1$ is other than benzyl and when $R^{2a}$ and $R^{2b}$ are each phenyl, and X and Y are each Cl, then $R^1$ is other than methyl or ethyl. Particularly preferred is a composition comprising the compound of Formula II wherein $R^{2a}$ and $R^{2b}$ are each H, X is Br, Y is Cl and $R^1$ is methyl. Also particularly preferred is a composition comprising the compound of Formula II wherein $R^{2a}$ and $R^{2b}$ are each H, X is Br, Y is Cl and $R^1$ is ethyl. This invention also pertains to the compounds of Formula II comprised by said compositions, including preferred compositions and compositions of note.

Compounds of Formula VI can be prepared by a variety of chemical routes disclosed in the literature. For example, the compound of Formula VI wherein $R^{2a}$ and $R^{2b}$ are H, X is Br and $R^1$ is ethyl can be prepared as described by U. Aeberhard et al., *Helv. Chim. Acta* 1983, 66, 2740-2759. The compound of Formula VI wherein $R^{2a}$ and $R^{2b}$ are H, X is Cl and $R^1$ is benzyl can be prepared as described by J. E. Baldwin et al., *Tetrahedron* 1985, 41, 5241. Compounds of Formula VI wherein $R^{2a}$ and $R^{2b}$ are H and X is $OS(O)_2Me$, and $R^1$ is methyl, ethyl, isopropyl or benzyl can be prepared as described by S. C. Arnold & R. W. Lenz, *Makromol. Chem. Macromol. Symp.* 1986, 6, 285-303 and K. Fujishiro et al., Liquid Crystals 1992, 12 (3), 417-429. One skilled in the art appreciates that these example routes can be generalized. Of special interest is the compound of Formula VI wherein $R^{2a}$ and $R^{2b}$ are H, X is Br and $R^1$ is methyl, because its crystalline nature facilitates purification. Therefore the present invention also relates to a crystalline composition (e.g., crystals) comprising at least about 90% by weight, preferably at least about 95% by weight, of the compound of Formula VI wherein $R^{2a}$ and $R^{2b}$ are H, X is Br and $R_1$ is methyl. Impurities in said crystalline composition can for example comprise regioisomers of the Formula VI compound and/or the solvent of crystallization entrained in the crystal lattice.

Compounds of Formula III can be prepared by a wide variety of methods reported in the literature, for example, see G. H. Coleman in *Org. Syn.* Coll. Vol. I, 1941, 442-445 (L is aryl); O. Diels, *Chem. Ber.* 1914, 47, 2183-2195 (L is —C(O) $R^3$); L. F. Audrieth & L. H. Diamond, J. Am. Chem. Soc. 1954, 76, 4869-4871 (L is tertiary alkyl); L. Friedman et al. in *Org. Syn.* 1960, 40, 93-95 (L is $S(O)_2R^3$); and V. S. Sauro & M. S. Workentin, *Can. J. Chem.* 2002, 80, 250-262 (L is $P(O)(R3)_2$). It is believed that one skilled in the art using the preceding description can utilize the present invention to its fullest extent. The following Example is, therefore, to be construed as merely illustrative, and not limiting of the disclosure in any way whatsoever. Steps in the following Example illustrate a procedure for each step in an overall synthetic transformation, and the starting material for each step may not have necessarily been prepared by a particular preparative run whose procedure is described in other Examples or Steps. Percentages are by weight except for chromatographic solvent mixtures or where otherwise indicated. Parts and percentages for chromatographic solvent mixtures are by volume unless otherwise indicated. $^1$H NMR spectra are reported in ppm downfield from tetramethylsilane; "s" means singlet, "d" means doublet, "t" means triplet, "q" means quartet, "m" means multiplet, "dd" means doublet of doublets, "dt" means doublet of triplets, and "br s" means broad singlet. "ABX" refers to a $^1$H NMR three-proton spin system in which two protons "A" and "B" have a chemical shift difference that is relatively small compared to their spin-spin coupling and the third proton "X" has a chemical shift with a relatively large difference compared to the spin-spin coupling with protons "A" and "B".

EXAMPLE 1

Preparation of methyl 2-(3-chloro-2-pyridinyl)-5-oxo-3-pyrazolidinecarboxylate (Formula I wherein $R^1$ is methyl, $R^{2a}$ and $R^{2b}$ are H and L is 3-chloro-2-pyridinyl)

Step A: Preparation of 1-methyl hydrogen bromobutanedioate

Methyl hydrogen (2Z)-2-butendioate (also known as the monomethyl ester of maleic acid) (50 g, 0.385 mol) was added dropwise to a solution of hydrogen bromide in acetic acid 141.43 g, 33%, 0.577 mol) at 0° C. over 1 h. The reaction mixture was stored at about 5° C. overnight. The solvent was then removed under reduced pressure. Toluene (100 mL) was added, and the mixture was evaporated under reduced pressure. The process was repeated three times using more toluene (3×100 mL). Then toluene (50 mL) was added, and the mixture was cooled to −2° C. Hexanes (50 mL) was added dropwise to the mixture. When the addition was complete the mixture was stirred about 30 minutes while the product crystallized. The product was then isolated by filtration and dried in vacuo to provide the title compound as a white solid (63.37 g, 81.8% yield). A sample recrystallized from toluene/hexanes melted at 38-40° C.

IR (nujol): 1742, 1713, 1444, 1370, 1326, 1223, 1182, 1148, 1098, 996, 967, 909, 852 cm$^{-1}$.

$^1$H NMR (CDCl$_3$) δ 4.57 (X of ABX pattern, J=6.1, 8.9 Hz, 1H), 3.81 (s, 3H), 3.35 (½ of AB in ABX pattern, J=8.8, 17.7 Hz, 1H), 3.05 (½ of AB in ABX pattern, J=6.1, 17.8 Hz, 1H).

Step B: Preparation of methyl 2-bromo-4-chloro4-oxobutanoate

Thionyl chloride (6.54 g, 54.9 mmol) in dichloromethane (7 mL) was added dropwise over 30 minutes to a mixture of 1-methyl hydrogen bromobutanedioate (i.e. the product of Step A) (10 g, 47.4 mmol) and N,N-dimethylformamide (5 drops) in dichloromethane (20 mL) heated at reflux. The mixture was heated at reflux for an additional 60 minutes and then allowed to cool to room temperature. The solvent was removed under reduced pressure to leave the title product as an oil (11 g, about 100% yield).

IR (nujol): 3006, 2956, 1794, 1743, 1438, 1392, 1363, 1299, 1241, 1153, 1081, 977, 846, 832 cm$^{-1}$.

$^1$H NMR (CDCl$_3$) δ 4.56 (X of ABX pattern, J=5.8, 8.5 Hz, 1H), 3.87-3.78 (m, 4H), 3.53 (½ of AB in ABX pattern, J=6, 18.5 Hz, 1H).

Step C: Preparation of methyl 2-(3-chloro-2-pyridinyl)-5-oxo-3-pyrazolidine-carboxylate The crude product of Step B (i.e. methyl 2-bromo4-chloro4-oxobutanoate) (11.00 g, ~47.4 mmol) in acetonitrile (25 mL) was added over 65 minutes to a mixture of 3-chloro-2(1H)-pyridinone hydrazone (alternatively named (3-chloro-pyridin-2-yl)-hydrazine) (6.55 g, 45.6 mmol) and sodium bicarbonate (9.23 g, 0.110 mol) in acetonitrile (60 mL) at 0° C. The mixture was then allowed to warm to room temperature and was stirred for 3 h. The mixture was then warmed and maintained at 38° C. for 8 h. Then the mixture was allowed to cool, and the solvent was removed by evaporation under reduced pressure. Water (25 mL) was added, and acetic acid (about 1.9 mL) was added until the slurry had a pH of about 5. After 2 h, the product was isolated by filtration, rinsed with water (10 mL) and dried in vacuo to provide the title compound as a pale yellow solid (11 g, 89.8% yield). A sample recrystallized from ethanol melted at 147-148° C.

IR (nujol): 1756, 1690, 1581, 1429, 1295, 1202, 1183, 1165, 1125, 1079, 1032, 982, 966, 850, 813 cm$^{-1}$.

$^1$H NMR (DMSO-d$_6$) δ 10.16 (s, 1H), 8.27 (dd, J=1.4, 4.6 Hz, 1H), 7.93 (dd, J=1.6, 7.8 Hz, 1H), 7.19 (dd, J=4.6, 7.8 Hz, 1H), 4.87 (X of ABX pattern, J=1.6, 9.6 Hz, 1H), 3.73 (s, 3H), 2.90 (½ of AB in ABX pattern, J=9.7, 16.7 Hz, 1H), 2.38 (½ of AB in ABX pattern, J=1.6, 16.9 Hz, 1H).

By the procedures described herein together with methods known in the art, the compounds of Formulae II and III can be converted to compounds of Formula I as illustrated for Formulae Ia, IIa and IIIa in Table 1 and more generally for Formulae I, II and III in Table 2. The following abbreviations are used in the Tables: t is tertiary, s is secondary, n is normal, i is iso, Me is methyl, Et is ethyl, Pr is propyl, i-Pr is isopropyl, t-Bu is tertiary butyl, Ph is phenyl and Bn is benzyl (—CH$_2$Ph).

TABLE 1

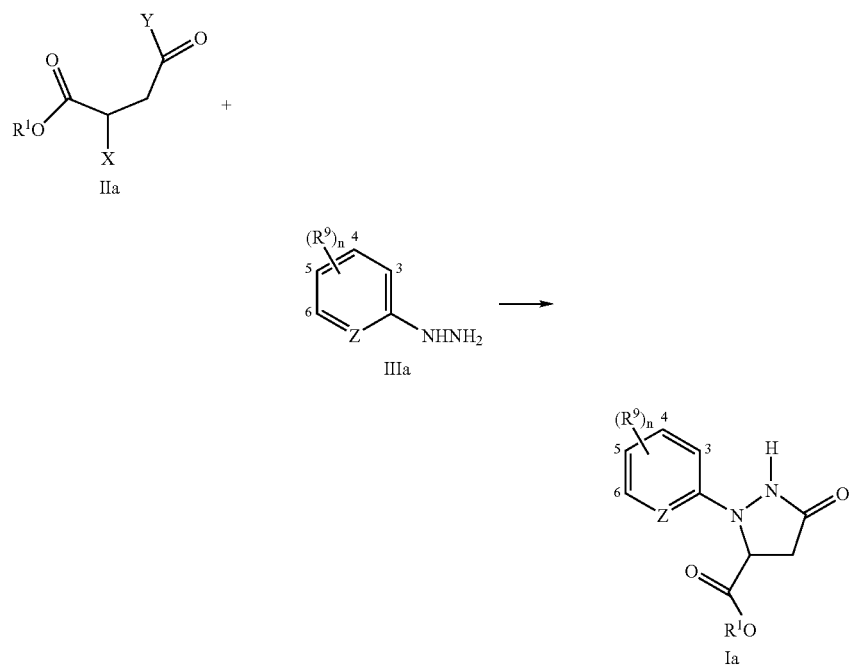

| X is Br; Y is Cl ||||||||||||
|---|---|---|---|---|---|---|---|---|---|---|---|
| R¹ is Me || R¹ is Et || R¹ is t-Bu || R¹ is Bn ||||||
| $(R^9)_n$ | Z | $(R^9)_n$ | Z | $(R^9)_n$ | Z | $(R^9)_n$ | Z | $(R^9)_n$ | Z | $(R^9)_n$ | Z |
| 3-Cl | N | 3-Cl | CCl | 3-Cl | N | 3-Cl | CCl | 3-Cl | N | 3-Cl | CCl |
| 3-Br | N | 3-Br | CCl | 3-Br | N | 3-Br | CCl | 3-Br | N | 3-Br | CCl |
| 3-Cl | CH | 3-Cl | CBr | 3-Cl | CH | 3-Cl | CBr | 3-Cl | CH | 3-Cl | CBr |
| 3-Br | CH | 3-Br | CBr | 3-Br | CH | 3-Br | CBr | 3-Br | CH | 3-Br | CBr |

| X is Cl; Y is Cl ||||||||||||
|---|---|---|---|---|---|---|---|---|---|---|---|
| R¹ is Me || R¹ is Et || R¹ is t-Bu || R¹ is Bn ||||||
| $(R^9)_n$ | Z | $(R^9)_n$ | Z | $(R^9)_n$ | Z | $(R^9)_n$ | Z | $(R^9)_n$ | Z | $(R^9)_n$ | Z |
| 3-Cl | N | 3-Cl | CCl | 3-Cl | N | 3-Cl | CCl | 3-Cl | N | 3-Cl | CCl |
| 3-Br | N | 3-Br | CCl | 3-Br | N | 3-Br | CCl | 3-Br | N | 3-Br | CCl |
| 3-Cl | CH | 3-Cl | CBr | 3-Cl | CH | 3-Cl | CBr | 3-Cl | CH | 3-Cl | CBr |
| 3-Br | CH | 3-Br | CBr | 3-Br | CH | 3-Br | CBr | 3-Br | CH | 3-Br | CBr |

| X is OS(O)₂Me; Y is Cl ||||||||||||
|---|---|---|---|---|---|---|---|---|---|---|---|
| R¹ is Me || R¹ is Et || R¹ is t-Bu || R¹ is Bn ||||||
| $(R^9)_n$ | Z | $(R^9)_n$ | Z | $(R^9)_n$ | Z | $(R^9)_n$ | Z | $(R^9)_n$ | Z | $(R^9)_n$ | Z |
| 3-Cl | N | 3-Cl | CCl | 3-Cl | N | 3-Cl | CCl | 3-Cl | N | 3-Cl | CCl |
| 3-Br | N | 3-Br | CCl | 3-Br | N | 3-Br | CCl | 3-Br | N | 3-Br | CCl |
| 3-Cl | CH | 3-Cl | CBr | 3-Cl | CH | 3-Cl | CBr | 3-Cl | CH | 3-Cl | CBr |
| 3-Br | CH | 3-Br | CBr | 3-Br | CH | 3-Br | CBr | 3-Br | CH | 3-Br | CBr |

| X is OS(O)2Ph; Y is Cl ||||||||||||
|---|---|---|---|---|---|---|---|---|---|---|---|
| R¹ is Me || R¹ is Et || R¹ is t-Bu || R¹ is Bn ||||||
| $(R^9)_n$ | Z | $(R^9)_n$ | Z | $(R^9)_n$ | Z | $(R^9)_n$ | Z | $(R^9)_n$ | Z | $(R^9)_n$ | Z |
| 3-Cl | N | 3-Cl | CCl | 3-Cl | N | 3-Cl | CCl | 3-Cl | N | 3-Cl | CCl |
| 3-Br | N | 3-Br | CCl | 3-Br | N | 3-Br | CCl | 3-Br | N | 3-Br | CCl |
| 3-Cl | CH | 3-Cl | CBr | 3-Cl | CH | 3-Cl | CBr | 3-Cl | CH | 3-Cl | CBr |
| 3-Br | CH | 3-Br | CBr | 3-Br | CH | 3-Br | CBr | 3-Br | CH | 3-Br | CBr |

TABLE 1-continued

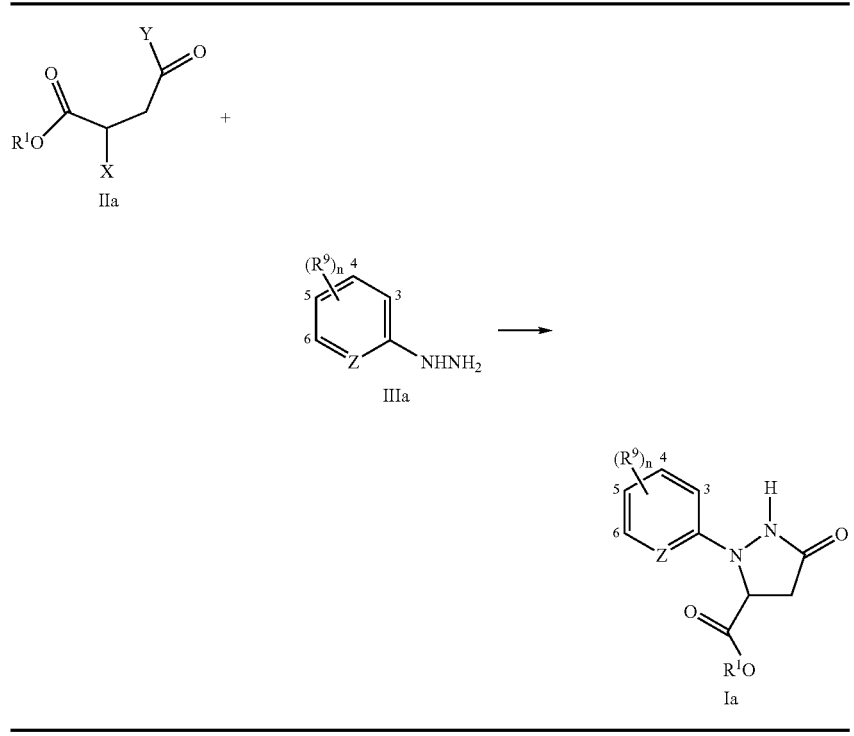

| (R⁹)ₙ | R¹ | Z | (R⁹)ₙ | R¹ | Z | (R⁹)ₙ | R¹ | Z | (R⁹)ₙ | R¹ | Z |
|---|---|---|---|---|---|---|---|---|---|---|---|
| | | | | X is Br; Y is Cl | | | | | | | |
| 5-Cl | Me | CH | 3-OEt | Me | N | 4-I | Me | CH | 5-CF₂H | Me | CH |
| 4-n-Bu | Et | N | 2-OCF₃ | Et | N | 3-CN | Et | CH | 6-CH₃ | Et | N |
| 5-NMe₂ | n-Pr | CH | 3-cyclo-Pr | n-Pr | CH | 3-NO₂ | n-Pr | CH | 3-CH₂CF₃ | n-Pr | CH |
| 3-OCH₂F | i-Pr | N | H | i-Pr | N | 3-S(O)₂CH₃ | i-Pr | CH | 6-cyclohexyl | i-Pr | CH |
| 4-OCH₃ | n-Bu | CH | 4-F | n-Bu | CCl | 4-SCH₃ | n-Bu | CH | 4-CH₂CH=CH₂ | n-Bu | CH |
| 3-Me | s-Bu | N | 4-Me | i-Bu | CH | 3-Br | Bn | N | 3-CF₃ | t-Bu | N |

| (R⁹)ₙ is 3-Br; Z is CBr | | | | | | | | | | | |
|---|---|---|---|---|---|---|---|---|---|---|---|
| R¹ is Me | | | | R¹ is Et | | | | R¹ is n-Bu | | | |
| X | Y | X | Y | X | Y | X | Y | X | Y | X | Y |
| Cl | Br | I | Cl | Cl | Br | I | Cl | Cl | Br | I | Cl |
| Br | Br | OS(O)₂Ph-4-Me | Cl | Br | Br | OS(O)₂Ph-4-Me | Cl | Br | Br | OS(O)₂Ph-4-Me | Cl |
| Br | I | OS(O)₂CF₃ | Cl | Br | I | OS(O)₂CF₃ | Cl | Br | I | OS(O)₂CF₃ | Cl |
| Br | F | OS(O)₂CH₂CH₃ | Cl | Br | F | OS(O)₂CH₂CH₃ | Cl | Br | F | OS(O)₂CH₂CH₃ | Cl |

| (R⁹)ₙ is 3-Cl; Z is N | | | | | | | | | | | |
|---|---|---|---|---|---|---|---|---|---|---|---|
| R¹ is Me | | | | R¹ is Et | | | | R¹ is n-Bu | | | |
| X | Y | X | Y | X | Y | X | Y | X | Y | X | Y |
| Cl | Br | I | Cl | Cl | Br | I | Cl | Cl | Br | I | Cl |
| Br | Br | OS(O)₂Ph-4-Me | Cl | Br | Br | OS(O)₂Ph-4-Me | Cl | Br | Br | OS(O)₂Ph-4-Me | Cl |
| Br | I | OS(O)₂CF₃ | Cl | Br | I | OS(O)₂CF₃ | Cl | Br | I | OS(O)₂CF₃ | Cl |
| Br | F | OS(O)₂CH₂CH₃ | Cl | Br | F | OS(O)₂CH₂CH₃ | Cl | Br | F | OS(O)₂CH₂CH₃ | Cl |

TABLE 2

$$\text{II} + \text{LNHNH}_2 \longrightarrow \text{II}$$
(III)

| R²ᵃ | R²ᵇ | L | R²ᵃ | R²ᵇ | L |
|---|---|---|---|---|---|
| \multicolumn{6}{c}{R¹ is Me, X is Br, Y is Cl} |

| R²ᵃ | R²ᵇ | L | R²ᵃ | R²ᵇ | L |
|---|---|---|---|---|---|
| H | H | Ph-4-Me | H | H | —P(O)(OMe)₂ |
| Me | H | Ph | H | H | —P(O)(OMe)Ph |
| OMe | H | Ph | H | H | —P(O)Et₂ |
| Me | Me | Ph-2-Cl | H | H | —C(CH₃)₂(CH₂)₂CH₃ |
| H | H | 3-thienyl | H | H | —C(CH₃)₂CF₃ |
| H | H | t-Bu | H | H | —C(CH₃)₂CH₂OCH₃ |
| H | H | —C(O)Ph | Me | H | Ph-3-OMe |
| H | H | —C(O)OMe | Ph | Ph | Ph |
| H | H | —C(O)N(Me)Et | CH₂CF₃ | H | 2-napthyl |
| H | H | —S(O)₂Me | O-allyl | H | Ph |
| H | H | —S(O)₂Ph-4-Me | Me | CH₂OCH₃ | Ph-2,4-di-Me |
| H | H | Ph-Ph-4-Me | —(CH₂)₄— | | Ph |
| H | 2-thienyl | Ph-3-OMe | —(CH₂)₂O(CH₂)₂— | | Ph-4-i-Pr |
| H | H | Ph | | | |

| R²ᵃ | R²ᵇ | L | R²ᵃ | R²ᵇ | L |
|---|---|---|---|---|---|
| \multicolumn{6}{c}{R¹ is Et, X is Br, Y is Cl} |

| R²ᵃ | R²ᵇ | L | R²ᵃ | R²ᵇ | L |
|---|---|---|---|---|---|
| H | H | Ph-3-Cl | H | H | —P(O)(OEt)₂ |
| Et | H | Ph | H | H | —P(O)(OEt)Ph-4-Me |
| OEt | H | Ph | H | H | —P(O)Me₂ |
| Me | n-Pr | Ph-2-Me | H | H | —C(CH₃)₂(CH₂)₄CH₃ |
| H | H | 3-thienyl-2-Me | H | H | —C(CH₃)₂CH₂CF₃ |
| Me | H | t-Bu | H | H | —C(CH₂CH₃)₂CH₃ |
| H | H | —C(O)Ph-4-Cl | Et | H | Ph-3-OMe |
| H | H | —C(O)OCH₂CH₂OCH₃ | Ph | Ph | Ph-4-OEt |
| H | H | —C(O)N(Me)₂ | H | H | 1-napthyl |
| H | H | —S(O)₂Me | O-allyl | H | Ph-4-Me |
| H | H | —S(O)₂Ph-3-Br | Me | CH₂OCH₃ | Ph-2,4-di-Cl |
| H | H | Ph-Ph-4-Cl | —(CH₂)₄— | | Ph-3-F |
| H | 2-thienyl | Ph-4-OMe | —(CH₂)₂O(CH₂)₂— | | Ph-4-CH(CH₃)₂ |
| H | H | Ph | | | |

Among the compounds preparable according to the method of the present invention, compounds of Formula Ia are particularly useful for preparing compounds of Formula IV

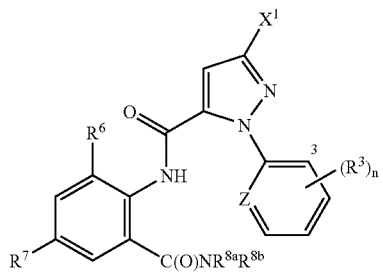

wherein Z, $R^3$ and n are defined as above; $X^1$ is halogen; $R^6$ is $CH_3$, F, Cl or Br; $R^7$ is F, Cl, Br, I, CN or $CF_3$; $R^{8a}$ is H or $C_1$-$C_4$ alkyl; and $R^{8b}$ is H or $CH_3$. Preferably Z is N, n is 1, and $R^3$ is Cl or Br and is at the 3-position.

Compounds of Formula IV are useful as insecticides, as described, for example, in PCT Publication No. WO 01/70671, published Sep. 27, 2001, PCT Publication No. WO 03/015519, published Feb. 27, 2003, and PCT Publication No. WO 03/015518, published Feb. 27, 2003, as well as in U.S. patent. application Ser. No. 60/323,941, filed Sep. 21, 2001, the disclosure of which was substantively published on Mar. 27, 2003 in PCT Publication No. WO 03/024222. The preparation of compounds of Formula 9 and Formula IV is described in U.S. patent application Ser. No. 60/446451, filed Feb. 11, 2003 and U.S. patent application Ser. No. 60/446438, filed Feb. 11, 2003, and hereby incorporated herein in their entirety by reference; as well as in PCT Publication No. WO 03/016283, published Feb. 27, 2003.

Compounds of Formula IV can be prepared from corresponding compounds of Formula Ia by the processes outlined in Schemes 6-11.

As illustrated in Scheme 6, a compound of Formula Ia is treated with a halogenating reagent, usually in the presence of a solvent to provide the corresponding halo compound of Formula 6.

Scheme 6

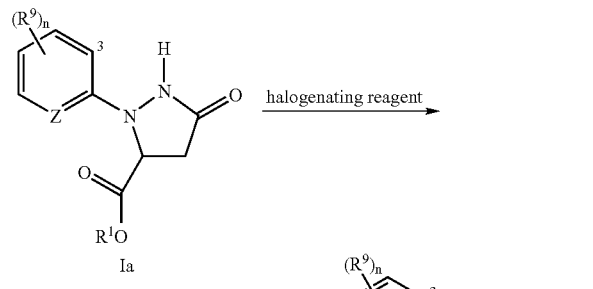

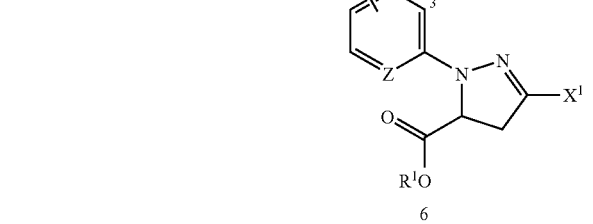

wherein $R^1$, $R^9$, Z and n are as previously defined, and $X^1$ is halogen.

Halogenating reagents that can be used include phosphorus oxyhalides, phosphorus trihalides, phosphorus pentahalides, thionyl chloride, dihalotrialkylphosphoranes, dihalodiphenylphosphoranes, oxalyl chloride, phosgene, sulfur tetrafluoride and (diethylamino)sulfur trifluoride. Preferred are phosphorus oxyhalides and phosphorus pentahalides. To obtain complete conversion, at least 0.33 equivalents of phosphorus oxyhalide versus the compound of Formula Ia (i.e. the mole ratio of phosphorus oxyhalide to Formula Ia is at least 0.33) should be used, preferably between about 0.33 and 1.2 equivalents. To obtain complete conversion, at least 0.20 equivalents of phosphorus pentahalide versus the compound of Formula Ia should be used, preferably between about 0.20 and 1.0 equivalents. Typical solvents for this halogenation include halogenated alkanes, such as dichloromethane, chloroform, chlorobutane and the like, aromatic solvents, such as benzene, xylene, chlorobenzene and the like, ethers, such as tetrahydrofuran, p-dioxane, diethyl ether, and the like, and polar aprotic solvents such as acetonitrile, N,N-dimethylformamide, and the like. Optionally, an organic base, such as triethylamine, pyridine, N,N-dimethylaniline or the like, can be added. Addition of a catalyst, such as N,N-dimethylformamide, is also an option. Preferred is the process in which the solvent is acetonitrile and a base is absent. Typically, neither a base nor a catalyst is required when acetonitrile solvent is used. The preferred process is conducted by mixing the compound of Formula Ia in acetonitrile. The halogenating reagent is then added over a convenient time, and the mixture is then held at the desired temperature until the reaction is complete. The reaction temperature is typically between about 20° C. and the boiling point of acetonitrile, and the reaction time is typically less than 2 hours. The reaction mass is then neutralized with an inorganic base, such as sodium bicarbonate, sodium hydroxide and the like, or an organic base, such as sodium acetate. The desired product, a compound of Formula 6, can be isolated by methods known to those skilled in the art, including extraction, crystallization and distillation.

Alternatively as shown in Scheme 7, compounds of Formula 6 wherein $X^1$ is halogen such as Br or Cl can be prepared by treating the corresponding compounds of Formula 6a wherein $X^2$ is a different halogen (e.g., Cl for making Formula 6 wherein $X^1$ is Br) or a sulfonate group such as methanesulfonate, benzenesulfonate or p-toluenesulfonate with hydrogen bromide or hydrogen chloride, respectively.

Scheme 7

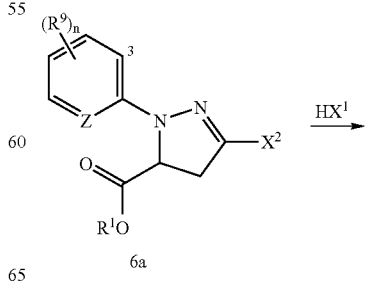

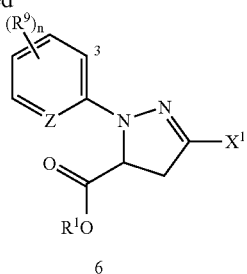

6 wherein $R^1$, $R^9$ and n are as previously defined for Formula Ia. By this method the $X^2$ halogen or sulfonate substituent on the Formula 6a starting compound is replaced with Br or Cl from hydrogen bromide or hydrogen chloride, respectively. The reaction is conducted in a suitable solvent such as dibromomethane, dichloromethane, acetic acid, ethyl acetate or acetonitrile. The reaction can be conducted at or near atmospheric pressure or above atmospheric pressure in a pressure vessel. The hydrogen halide starting material can be added in the form of a gas to the reaction mixture containing the Formula 6a starting compound and solvent. When $X^2$ in the starting compound of Formula 6a is a halogen such as Cl, the reaction is preferably conducted in such a way that the hydrogen halide generated from the reaction is removed by sparging or other suitable means. Alternatively, the hydrogen halide starting material can be first dissolved in an inert solvent in which it is highly soluble (such as acetic acid) before contacting with the starting compound of Formula 6a either neat or in solution. Also when $X^2$ in the starting compound of Formula 6a is a halogen such as Cl, substantially more than one equivalent of hydrogen halide starting material (e.g., 4 to 10 equivalents) is typically needed depending upon the level of conversion desired. One equivalent of hydrogen halide starting material can provide high conversion when $X^2$ in the starting compound of Formula 6a is a sulfonate group, but when the starting compound of Formula 6a comprises at least one basic function (e.g., a nitrogen-containing heterocycle), more than one equivalent of hydrogen halide starting material is typically needed. The reaction can be conducted between about 0 and 100° C., most conveniently near ambient temperature (e.g., about 10 to 40° C.), and more preferably between about 20 and 30° C. Addition of a Lewis acid catalyst (such as aluminum tribromide for preparing Formula 6 wherein $X^1$ is Br) can facilitate the reaction. The product of Formula 6 is isolated by the usual methods known to those skilled in the art, including extraction, distillation and crystallization.

Starting compounds of Formula 6a wherein $X^2$ is Cl or Br are also of Formula 6 and can be prepared from corresponding compounds of Formula Ia as already described for Scheme 6. Starting compounds of Formula 6a wherein $X^2$ is a sulfonate group can likewise be prepared from corresponding compounds of Formula Ia by standard methods such as treatment with a sulfonyl chloride (e.g., methanesulfonyl chloride, benzenesulfonyl chloride or p-toluenesulfonyl chloride) and base in a suitable solvent. Suitable solvents include dichloromethane, tetrahydrofuran, acetonitrile and the like. Suitable bases include tertiary amines (e.g., triethylamine, N,N-diisopropylethylamine) and ionic bases such as potassium carbonate and the like. A tertiary amine is preferred as the base. At least one of equivalent (preferably a small excess, e.g., 5-10%) of the sulfonyl chloride compound and the base relative to the compound Formula Ia is generally used to give complete conversion. The reaction is typically conducted at a temperature between about −50° C. and the boiling point of the solvent, more commonly between about 0° C. and ambient temperature (i.e. about 15 to 30° C.). The reaction is typically complete within a couple hours to several days; the progress of the reaction can by monitored by such techniques known to those skilled in the art as thin layer chromatography and analysis of the $^1H$ NMR spectrum. The reaction mixture is then worked up, such as by washing with water, drying the organic phase and evaporating the solvent. The desired product, a compound of Formula 6a wherein $X^2$ is a sulfonate group, can be isolated by methods known to those skilled in the art, including extraction, crystallization and distillation.

As illustrated in Scheme 8, a compound of Formula 6 is then treated with an oxidizing agent optionally in the presence of acid.

Scheme 8

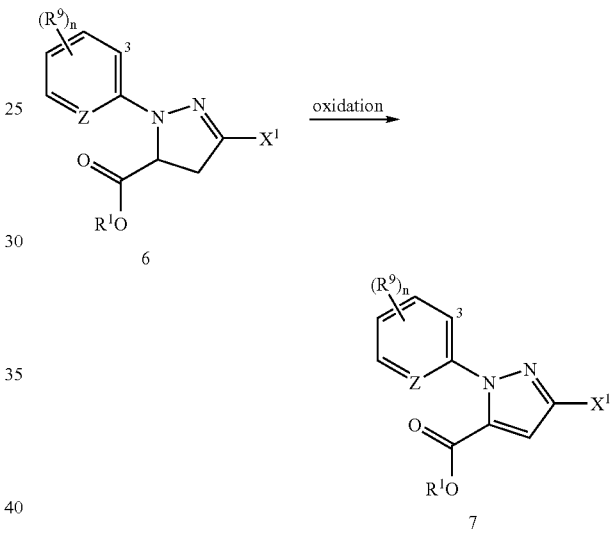

wherein $R^1$, $R^9$, Z, $X^1$ and n are as previously defined for Formula 6 in Scheme 6.

A compound of Formula 6 wherein $R^1$ is $C_1$-$C_4$ alkyl is preferred as starting material for this step. The oxidizing agent can be hydrogen peroxide, organic peroxides, potassium persulfate, sodium persulfate, ammonium persulfate, potassium monopersulfate (e.g., Oxone®) or potassium permanganate. To obtain complete conversion, at least one equivalent of oxidizing agent versus the compound of Formula 6 should be used, preferably from about one to two equivalents. This oxidation is typically carried out in the presence of a solvent. The solvent can be an ether, such as tetrahydrofuran, p-dioxane and the like, an organic ester, such as ethyl acetate, dimethyl carbonate and the like, or a polar aprotic organic such as N,N-dimethylformamide, acetonitrile and the like. Acids suitable for use in the oxidation step include inorganic acids, such as sulfuric acid, phosphoric acid and the like, and organic acids, such as acetic acid, benzoic acid and the like. The acid, when used, should be used in greater than 0.1 equivalents versus the compound of Formula 6. To obtain complete conversion, one to five equivalents of acid can be used. For the compounds of Formula 6 wherein Z is $CR^{10}$, the preferred oxidant is hydrogen peroxide and the oxidation is preferably carried out in the absence of acid. For the compounds of Formula 6 wherein Z is N, the preferred oxidant is potassium persulfate and the oxidation is preferably carried out in the presence of sulfuric acid. The reaction can be carried out by mixing the compound of Formula 6 in the desired solvent and, if used, the acid. The oxidant can then be added at a convenient rate. The reaction temperature is typically varied from as low as about 0° C. up to the boiling point of the solvent in order to obtain a reasonable reaction time to complete the reaction, preferably less than 8 hours. The desired product, a compound of Formula 7 can be isolated by methods known to those skilled in the art, including extraction, chromatography, crystallization and distillation.

Carboxylic acid compounds of Formula 7 wherein $R^1$ is H can be prepared by hydrolysis from corresponding ester compounds of Formula 7 wherein, for example, $R^1$ is $C_1$-$C_4$ alkyl. Carboxylic ester compounds can be converted to carboxylic acid compounds by numerous methods including nucleophilic cleavage under anhydrous conditions or hydrolytic methods involving the use of either acids or bases (see T. W. Greene and P. G. M. Wuts, *Protective Groups in Organic Synthesis*, 2nd ed., John Wiley & Sons, Inc., New York, 1991, pp. 224-269 for a review of methods). For compounds of Formula 7, base-catalyzed hydrolytic methods are preferred. Suitable bases include alkali metal (such as lithium, sodium or potassium) hydroxides. For example, the ester can be dissolved in a mixture of water and an alcohol such as ethanol. Upon treatment with sodium hydroxide or potassium hydroxide, the ester is saponified to provide the sodium or potassium salt of the carboxylic acid. Acidification with a strong acid, such as hydrochloric acid or sulfuric acid, yields the carboxylic acid of Formula 7 wherein $R^1$ is H. The carboxylic acid can be isolated by methods known to those skilled in the art, including extraction, distillation and crystallization.

Coupling of a pyrazolecarboxylic acid of Formula 7 wherein $R^1$ is H with an anthranilic acid of Formula 8 provides the benzoxazinone of Formula 9. In Scheme 9, a benzoxazinone of Formula 9 is prepared directly via sequential addition of methanesulfonyl chloride in the presence of a tertiary amine such as triethylamine or pyridine to a pyrazolecarboxylic acid of Formula 7 wherein $R^1$ is H, followed by the addition of an anthranilic acid of Formula 8, followed by a second addition of tertiary amine and methanesulfonyl chloride.

Scheme 9

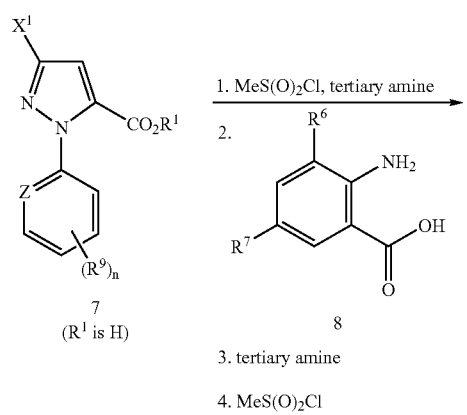

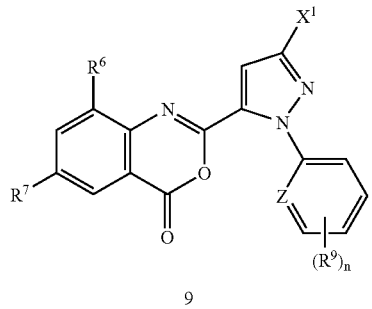

wherein $R^6$, $R^7$, $R^9$, $X^1$, Z and n are as defined for Formula IV. This procedure generally affords good yields of the benzoxazinone.

Scheme 10 depicts an alternate preparation for benzoxazinones of Formula 9 involving coupling of a pyrazole acid chloride of Formula 11 with an isatoic anhydride of Formula 10 to provide the Formula 9 benzoxazinone directly.

Scheme 10

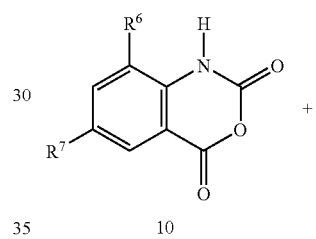

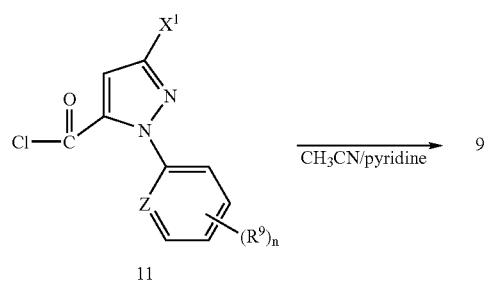

wherein $R^6$, $R^7$, $R^9$, $X^1$, Z and n are as defined for Formula IV. Solvents such as pyridine or pyridine/acetonitrile are suitable for this reaction. The acid chlorides of Formula 11 are available from the corresponding acids of Formula 7 wherein $R^1$ is H by known procedures such as chlorination with thionyl chloride or oxalyl chloride.

Compounds of Formula IV can be prepared by the reaction of benzoxazinones of Formula 9 with $C_1$-$C_4$ alkylamines and ($C_1$-$C_4$ alkyl)(methyl)amines of Formula 12 as outlined in Scheme 11.

Scheme 11

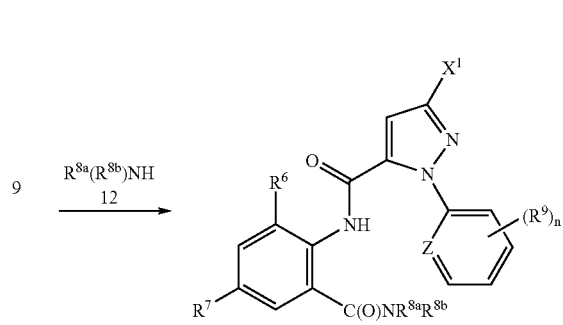

wherein R[6], R[7], R[8a], R[8b], R[9], X[1], Z and n are as previously defined.

The reaction can be run neat or in a variety of suitable solvents including acetonitrile, tetrahydrofuran, diethyl ether, dichloromethane or chloroform with optimum temperatures ranging from room temperature to the reflux temperature of the solvent. The general reaction of benzoxazinones with amines to produce anthranilamides is well documented in the chemical literature. For a review of benzoxazinone chemistry see Jakobsen et al., *Biorganic and Medicinal Chemistry* 2000, 8, 2095-2103 and references cited within. See also Coppola, *J. Heterocyclic Chemistry* 1999, 36, 563-588.

What is claimed is:

1. A method for preparing a 2-substituted-5-oxo-3-pyrazolidinecarboxylate compound of Formula I

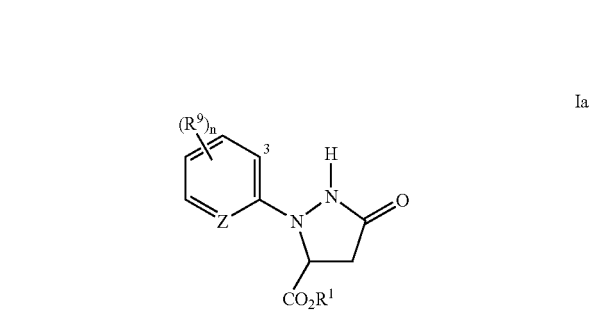

wherein
L is H, optionally substituted aryl, optionally substituted tertiary alkyl, —C(O)R[3], —S(O)$_2$R[3] or —P(O)(R[3])$_2$;
R[1] is an optionally substituted carbon moiety;
R[2a] is H, OR[4] or an optionally substituted carbon moiety;
R[2b] is H or an optionally substituted carbon moiety;
each R[3] is independently OR[5], N(R[5])$_2$ or an optionally substituted carbon moiety;
R[4] is an optionally substituted carbon moiety; and
each R[5] is selected from optionally substituted carbon moieties; comprising: contacting a succinic acid derivative of Formula II

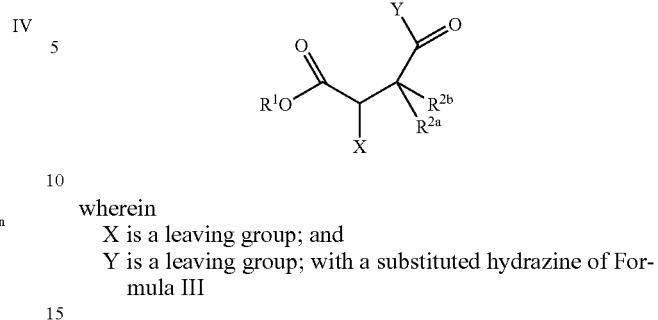

wherein
X is a leaving group; and
Y is a leaving group; with a substituted hydrazine of Formula III

LNHNH$_2$  III in the presence of a suitable acid scavenger and solvent.
2. The method of claim 1 wherein X is Cl, Br or I.
3. The method of claim 2 wherein X is Br.
4. The method of claim 1 wherein Y is Cl.
5. The method of claim 1 wherein R[1] is C$_1$-C$_4$ alkyl.
6. The method of claim 1 wherein the compound of Formula I is of Formula Ia

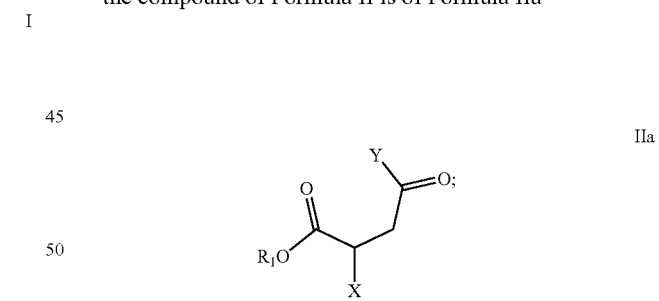

the compound of Formula II is of Formula IIa

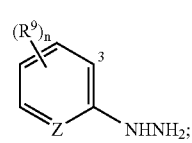

and the compound of Formula III is of Formula IIIa

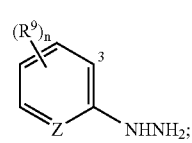

wherein
each R[9] is independently C$_1$-C$_4$ alkyl, C$_2$-C$_4$ alkenyl, C$_2$-C$_4$ alkynyl, C$_3$-C$_6$ cycloalkyl, C$_1$-C$_4$ haloalkyl, C$_2$-C$_4$ haloalkenyl, C$_2$-C$_4$ haloalkynyl, C$_3$-C$_6$ halocycloalkyl, halogen, CN, NO$_2$, C$_1$-C$_4$ alkoxy, C$_1$-C$_4$ haloalkoxy, C$_1$-C$_4$ alkylthio, C$_1$-C$_4$ alkylsulfinyl, C$_1$-C$_4$ alkylsulfonyl, C$_1$-C$_4$ alkylamino, C$_2$-C$_8$ dialkylamino, C$_3$-C$_6$ cycloalkylamino, (C$_1$-C$_4$ alkyl)(C$_3$-C$_6$ cycloalkyl)amino, C$_2$-C$_4$ alkylcarbonyl, C$_2$-C$_6$ alkoxycarbonyl, C$_2$-C$_6$ alkylaminocarbonyl, C$_3$-C$_8$ dialkylaminocarbonyl or C$_3$-C$_6$ trialkylsilyl;

Z is N or CR$^{10}$;

R$^{10}$ is H or R$^9$; and n is an integer from 0 to 3.

7. The method of claim 6 wherein X is Br.

8. The method of claim 6 wherein Y is Cl.

9. The method of claim 6 wherein R$^1$ is CH$_3$.

10. The method of claim 1 wherein methyl 2-(3-chloro-2-pyridinyl)-5-oxo-3-pyrazolidinecarboxylate is prepared by contacting methyl 2-bromo-4-chloro-4-oxobutanoate with (3-chloro-2-pyridin-2-yl)-hydrazine in the presence of sodium bicarbonate as the acid scavenger and acetonitrile as the solvent.

11. The method of claim 6 wherein the compound of Formula Ia is methyl 2-(3-chloro-2-pyridinyl)-5-oxo-3-pyrazolidinecarboxylate, the compound of Formula IIa is methyl 2-bromo-4-chloro-4-oxobutanoate and the compound of Formula IIIa is (3-chloro-2-pyridin-2-yl)-hydrazine.

12. The method of claim 11 wherein the acid scavenger is selected from the group consisting of sodium bicarbonate, sodium carbonate, sodium hydrogenphosphate and sodium phosphate.

13. The method of claim 12 wherein the solvent is selected from the group consisting of nitrile solvents.

* * * * *